United States Patent
Kobayashi

(10) Patent No.: US 7,852,334 B2
(45) Date of Patent: Dec. 14, 2010

(54) ULTRASONIC IMAGING APPARATUS, AN IMAGE-PROCESSING APPARATUS, AND AN ULTRASONIC IMAGE-PROCESSING METHOD

(75) Inventor: Tadaharu Kobayashi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 824 days.

(21) Appl. No.: 11/760,341

(22) Filed: Jun. 8, 2007

(65) Prior Publication Data
US 2007/0285421 A1    Dec. 13, 2007

(30) Foreign Application Priority Data
Jun. 12, 2006    (JP) .............................. 2006-162444

(51) Int. Cl.
*G06T 15/00* (2006.01)

(52) U.S. Cl. ...................... 345/419; 345/505; 345/532; 382/173; 382/199; 600/437; 600/443

(58) Field of Classification Search ................ 345/505, 345/532, 419; 382/173, 199; 600/437, 443, 600/447
See application file for complete search history.

(56) References Cited

U.S. PATENT DOCUMENTS

| | | | |
|---|---|---|---|
| 4,885,703 A | 12/1989 | Deering | |
| 5,779,641 A | 7/1998 | Hatfield et al. | |
| 6,300,961 B1 * | 10/2001 | Finger et al. ................. | 345/505 |
| 6,482,159 B1 * | 11/2002 | Wiesauer et al. ............. | 600/443 |
| 6,530,885 B1 * | 3/2003 | Entrekin et al. ............. | 600/437 |
| 6,629,926 B1 * | 10/2003 | Finger et al. ................. | 600/437 |
| 7,223,240 B2 * | 5/2007 | Murashita .................... | 600/443 |
| 7,386,153 B2 * | 6/2008 | Kim ........................... | 382/128 |
| 7,567,993 B2 * | 7/2009 | Trimmer et al. ............. | 1/1 |

FOREIGN PATENT DOCUMENTS

| | | |
|---|---|---|
| EP | 0 513 474 A1 | 11/1992 |
| EP | 1 416 443 A1 | 5/2004 |
| JP | 2001-5996 | 1/2001 |
| JP | 2003-61956 | 3/2003 |

OTHER PUBLICATIONS

Kenneth R. Castleman, "Digital Image Processing", Trans. Tsuneo Saito. Tokyo: Science and Technology Press Inc, 2001, pp. 826-832 and 5 cover pages.

Marc Levoy, "Display of Surfaces from Volume Data", IEEE Computer Graphics and Applications, vol. 8 No. 3, XP-002312196, May 1998, pp. 29-37.

Thomas R. Nelson, et al., "Visualization of 3D Ultrasound Data", IEEE Computer Graphics & Applications, vol. 13 No. 6, XP-002454570, Nov. 1993, pp. 50-57.

* cited by examiner

*Primary Examiner*—Phu Nguyen
(74) *Attorney, Agent, or Firm*—Oblon, Spivak, McClelland, Maier & Neustadt, L.L.P.

(57) ABSTRACT

A transmitter/receiver obtains scanning data by transmitting ultrasonic waves to a subject to be examined and receiving reflected waves from the subject to be examined. An image processor converts the scanning data into image data represented by a predetermined coordinate system and applies a predetermined smoothing process to the image data. The image processor calculates the vector of each point, based on the image data after the smoothing process. The image processor generates three-dimensional image data by applying a ray-tracing process to the image data to which the smoothing process has not been applied, according to the vector.

19 Claims, 18 Drawing Sheets

FIG. 2        PRIOR ART
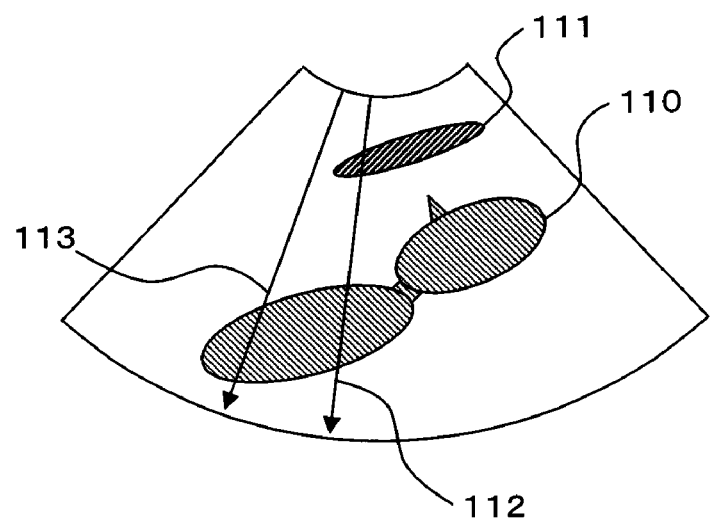
FIG. 3        PRIOR ART
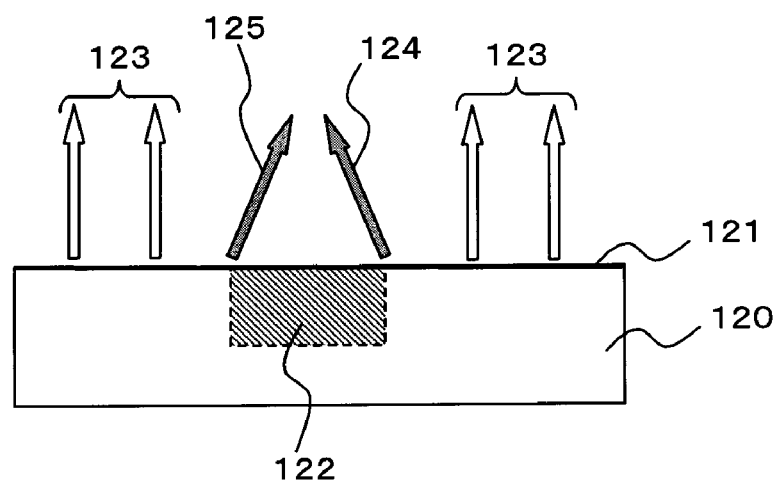

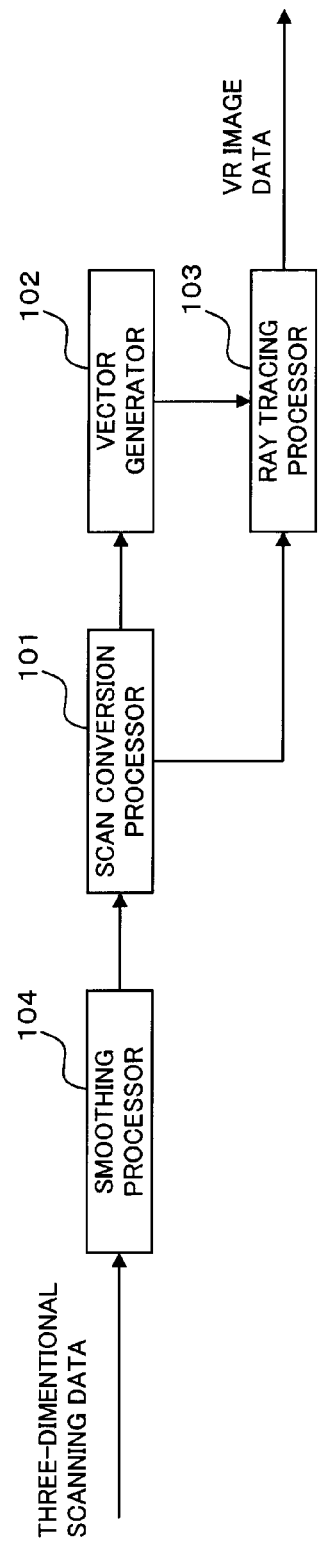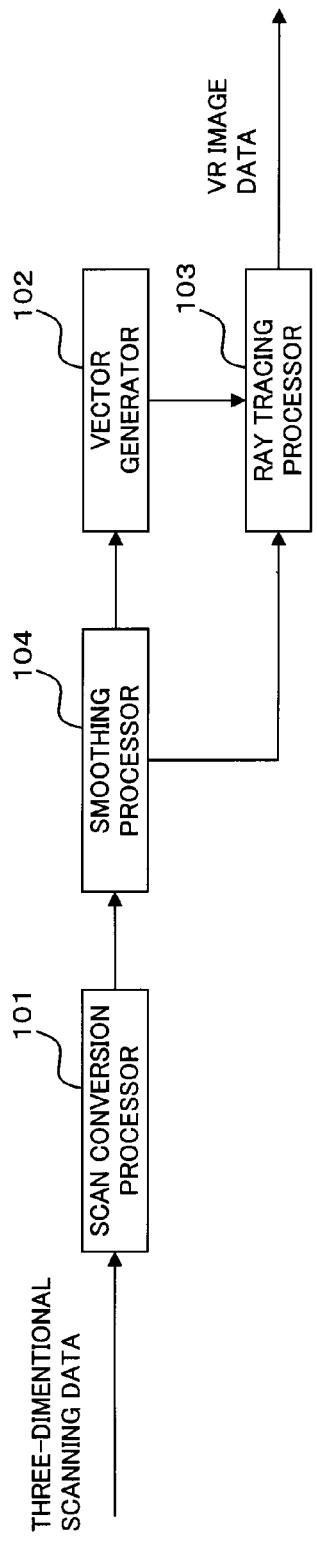

ULTRASONIC IMAGING APPARATUS, AN IMAGE-PROCESSING APPARATUS, AND AN ULTRASONIC IMAGE-PROCESSING METHOD

BACKGROUND OF THE INVENTION

1. Field of the Invention

The present invention relates to an ultrasonic imaging apparatus for obtaining three-dimensional image data, a medical image-processing apparatus, and an ultrasonic image-processing method.

2. Description of the Related Art

Diagnosis whereby a medical image diagnostic apparatus obtains a three-dimensional image of a subject to be examined and the three-dimensional image is used has become popular. For example, in diagnosis using ultrasonic waves, ultrasonic imaging apparatuses described in the following (1) through (3) are used.

(1) An ultrasonic imaging apparatus that comprises a two-dimensional array probe on which ultrasonic transducers are arranged two-dimensionally (in a lattice-like pattern) and that is capable of obtaining three-dimensional image data.

(2) An ultrasonic imaging apparatus that comprises a one-dimensional array probe on which ultrasonic transducers are arranged in a predetermined direction (scanning direction) and that is capable of obtaining data three-dimensionally by mechanically swinging the one-dimensional array probe.

(3) An ultrasonic imaging apparatus that is capable of obtaining data three-dimensionally by manually moving a one-dimensional array probe.

The ultrasonic imaging apparatus of (1) and the ultrasonic imaging apparatus of (2) described above can obtain three-dimensional scanning data by transmitting ultrasonic waves three-dimensionally and receiving the reflected waves. Scanning data that has been obtained three-dimensionally is converted into voxel data by applying a three-dimensional scan conversion process.

The ultrasonic imaging apparatus of (3) can obtain two-dimensional scanning data by transmitting ultrasonic waves two-dimensionally and receiving the reflected waves. The scanning data that has been obtained two-dimensionally is converted into two-dimensional image data by applying a two-dimensional scan conversion process. Furthermore, voxel data is generated, based on a plurality of two-dimensional image data.

Then, three-dimensional image data (may be referred to as "VR image data"), MPR image data in any cross-section, or the like is generated by applying image processing such as a volume rendering process (hereinafter, may be referred to as a VR process) or an MPR process (Multiplanar Reconstruction) to the voxel data.

In a shaded volume rendering process, the vector in each voxel constituting the voxel data is found. The method in which shaded three-dimensional image data is generated, based on the vector and the voxel data is known (e.g., Japanese Unexamined Patent Publication No. 2003-61956).

A process for generating three-dimensional data will now be described referring to FIG. 1. FIG. 1 is a block diagram showing a portion of an ultrasonic imaging apparatus according to a conventional art. The case of generating three-dimensional image data (VR image data), based on scanning data that has been obtained three-dimensionally (hereinafter, may be referred to as "three-dimensional scanning data") will be described herein.

Upon receiving three-dimensional scanning data obtained by transmitting/receiving ultrasonic waves three-dimensionally, a scan conversion processor 101 generates voxel data by applying a three-dimensional scan conversion process to the three-dimensional scanning data. Then, the scan conversion processor 101 outputs the voxel data to a vector generator 102 and a ray-tracing processor 103.

Upon receiving the voxel data from the scan conversion processor 101, the vector generator 102 finds the vector (direction) of each voxel. For example, the vector generator 102, for a certain voxel and voxels surrounding the voxel, finds the differentiation of the voxel values to find a tangent line in the voxel. Then, the vector generator 102 defines a vector perpendicular to the tangent line as the vector. Then, the vector generator 102 finds the vector of each voxel. In addition, the vector generator 102 normalizes the vector to convert the same into a unit vector. The "vector" is hereinafter described as indicating the "unit vector."

The vector of a voxel represents the direction of the surface of a structural object included in the voxel data. Therefore, it can be seen to which direction the surface of the structural object included in the voxel data is directed by finding the vector of the voxel.

Upon receiving voxel data from the scan conversion processor 101 and furthermore receiving the vector from the vector generator 102, the ray-tracing processor 103 generates three-dimensional image data by applying a ray-tracing process to the voxel data. The ray-tracing processor 103 finds the luminance (reflection brightness) at a certain point on an object surface, based on the direction of a ray from a light source set by the ray-tracing process and the orientation of the vector calculated by the vector generator 102, thereby generating a shaded three-dimensional image data (VR image data). Specifically, the ray-tracing processor 103 finds the luminance of the object surface by finding the inner product of a vector indicating the direction of the ray from the light source and the vector.

Meanwhile, because the ultrasonic imaging apparatus generates image data by transmitting ultrasonic waves into a subject to be examined and receiving the ultrasonic waves reflected by the subject to be examined, the scanning data to be obtained depends on the state of the path through which the ultrasonic waves propagate. The path through which the ultrasonic waves propagate will now be described referring to FIG. 2. FIG. 2 is a view for illustrating the path through which the ultrasonic waves propagate. For example, as shown in FIG. 2, even in the case of transmitting the ultrasonic waves to a phantom 110 made of uniform material, a difference arises in values of obtained scanning data, depending on the presence or absence of a structural object 111 in the path of ultrasonic beams, such as in the case of ultrasonic beam 112 and ultrasonic beam 113. The structural object 111 exists in the path of the ultrasonic beam 112, but the structural object 111 does not exist in the path of the ultrasonic beam 113, so that a difference arises in obtained data between the ultrasonic beam 112 and the ultrasonic beam 113.

Further, a difference arises in values of obtained scanning data, also depending on the depth where the phantom 110 is placed. Furthermore, in the ultrasonic imaging apparatus, a speckle noise arises due to interference of ultrasonic waves effects on an image.

As described above, in the ultrasonic imaging apparatus, the obtained voxels do not always have uniform voxel values, even when a subject to be examined made of uniform material is converted into an image, and the voxel value may change abruptly at a certain location.

Even in the case of transmission of ultrasonic waves to a spatially contiguous structural object, the voxel value to be obtained changes abruptly at a certain location. As causes thereof, the following factors (1) through (3) are conceivable.

(1) The reflection coefficient of ultrasonic waves changes, depending on the difference in material of the subject to be examined.

(2) There is a difference in the state of the path through which ultrasonic waves are transmitted and received.

(3) Speckle noise is generated.

Next, effects on three-dimensional image data (VR image data) when the voxel value changes abruptly on the surface of the spatially contiguous tissues (structural object) will be described.

As described above, the vector to be used to shade a three-dimensional image can be found by differentiation of voxel values. Therefore, at the location where the voxel value changes significantly, the orientation of the vector will significantly tilt with reference to the orientation of the normal voxel in the surrounding voxels.

This tilt of the vector will now be described referring to FIG. 3. FIG. 3 is a schematic drawing for illustrating the tilt of the vector. For example, when scanning data of a certain tissue 120 are obtained, if a site 122 exists in which the value of the scanning data changes abruptly on a surface 121, the orientations of vectors 124 and 125 of the surface 121 on which the site 122 exists will significantly tilt with reference to a vector 123 of another site. For example, if there is no concavity or convexity on the surface 121, the orientation of the vector is not supposed to tilt significantly. However, because there is a location where the value of the scanning data changes abruptly, the tilt of the vector at the location will significantly tilt with reference to the orientation of the vector at another location.

As described above, although the site 122 is spatially contiguous in the tissue 120, the value of the scanning data thereof changes more abruptly compared to those of other sites, so that the orientation of the vector on the surface where the site 122 exists will significantly tilt with reference to the orientation of the vector of the surrounding sites.

When a ray-tracing process is applied to voxel data by using the vector whose orientation significantly differs from those of the surrounding vectors, a strong shadow will be locally generated on a spatially contiguous (and smooth) structural object in response to the vector with a different orientation. That is, due to the orientation of the vector significantly tilting with reference to the orientation of the vector of another location, a strong shadow will occur even at the location where the shadow is not supposed to occur. Such a shadow is an artifact that should be removed, in obstetrical diagnosis and the like.

In order to remove the shadow (artifact) described above, a smoothing process has been conventionally applied to scanning data or voxel data. This smoothing process will be described referring to FIG. 4 and FIG. 5. FIG. 4 and FIG. 5 are block diagrams for illustrating the smoothing process according to the conventional art.

As shown in FIG. 4, for example, a smoothing processor 104 applies a smoothing process, by using a predetermined smoothing filter, to three-dimensional scanning data obtained by a scan. The scan conversion processor 101 generates voxel data by applying a three-dimensional scan conversion process to the scanning data after the smoothing process. The smoothing processor 104 calculates, for example, an average of scanning data included within a predetermined range.

In addition, as shown in FIG. 5, the smoothing processor 104 applies a smoothing process, by using a predetermined smoothing filter, to the voxel data generated by the scan conversion processor 101. The vector generator 102 calculates the vector of each voxel, based on the voxel data after the smoothing process. The ray-tracing processor 103 generates three-dimensional image data, based on the vector and the voxel data after the smoothing process. The smoothing processor 104 calculates, for example, an average of voxel values within a predetermined range.

However, when the intensity of the shadow (artifact) that should be removed is strong, it is necessary to apply a smoothing process by using a strong smoothing filter. For example, it is necessary to broaden a range in which the smoothing process is performed and to strengthen the smoothing actions. Thus, a smoothing process needs to be performed by using a strong smoothing filter, so that there is a problem in that space resolution of the three-dimensional image data obtained by volume rendering is markedly reduced. In other words, when a strong smoothing filter is used to remove the shadow as an artifact, there is a problem in that the three-dimensional image becomes a blurred image.

SUMMARY OF THE INVENTION

An object of the present invention is to provide an ultrasonic imaging apparatus, an image-processing apparatus and an ultrasonic image-processing method that are capable of lowering a shadow as an artifact without reducing the space resolution of three-dimensional image data.

In a first aspect of the present invention, an ultrasonic imaging apparatus comprises: a scanner configured to transmit ultrasonic waves to a subject to be examined and receive reflected waves from the subject to be examined; and an image processor configured to apply a process for smoothing the vector based on an output from the scanner and generate three-dimensional image data based on an output to which the smoothing process has not been applied, according to the orientation of the smoothed vector.

According to the first aspect of the present invention, generating three-dimensional image data based on an output to which a smoothing process has not been applied, according to the orientation of the smoothed vector, makes it possible to reduce shadows as artifacts without reducing the space resolution of the three-dimensional image data.

In a second aspect of the present invention, an ultrasonic imaging apparatus according to the first aspect of the present invention is characterized in that: the scanner obtains scanning data by transmitting the ultrasonic waves to the subject to be examined and receiving the reflected waves from the subject to be examined; and the image processor comprises: a converter configured to convert the scanning data into image data represented by a predetermined three-dimensional coordinate system; a smoothing processor configured to apply a smoothing process to the image data; a vector generator configured to calculate the vector of each point constituting the image data based on the image data to which the smoothing process has been applied; and a three-dimensional image generator configured to generate three-dimensional image data by applying a ray-tracing process to the image data to which the smoothing process has not been applied, according to the orientation of the vector.

According to the second aspect of the present invention, finding the vector of each point based on the image data to which a smoothing process has been applied and generating three-dimensional image data based on the image data to which a smoothing process has not been applied and the vector makes it possible to reduce shadows as artifacts without reducing the space resolution of the three-dimensional image data.

In a third aspect of the present invention, an ultrasonic imaging apparatus according to the first aspect of the present invention is characterized in that: the scanner obtains scanning data by transmitting the ultrasonic waves to the subject to be examined and receiving the reflected waves from the subject to be examined; and the image processor comprises: a converter configured to convert the scanning data into image data represented by a predetermined three-dimensional coordinate system; a vector generator configured to calculate the vector of each point constituting the image data based on the image data; an averaging processor configured to average the vector of each point by calculating the average of vectors for a plurality of vectors included within a predetermined range; and a three-dimensional image generator configured to generate three-dimensional image data by applying a ray-tracing process to the image data, according to the orientation of the averaged vector.

According to the third aspect of the present invention, averaging the vector and generating three-dimensional image data based on the image data to which a smoothing process has not been applied and the vector makes it possible to reduce shadows as artifacts without reducing the space resolution of the three-dimensional image data.

In a fourth aspect of the present invention, an ultrasonic imaging apparatus according to the first aspect of the present invention is characterized in that: the scanner obtains scanning data by transmitting the ultrasonic waves to the subject to be examined and receiving the reflected waves from the subject to be examined; and the image processor comprise: a smoothing processor configured to apply a smoothing process to the scanning data; a converter configured to convert the scanning data to which said smoothing process has not been applied into first image data represented by a predetermined three-dimensional coordinate system, and furthermore convert the scanning data to which the smoothing process has been applied into second image data represented by a predetermined three-dimensional coordinate system; a vector generator configured to calculate the vector of each point constituting the second image data based on the second image data; a three-dimensional image generator configured to generate three-dimensional image data by applying a ray-tracing process to the first image data, according to the orientation of the vector.

According to the fourth aspect of the present invention, finding the vector of each point based on the scanning data to which a smoothing process has been applied and generating three-dimensional image data based on the image data to which a smoothing process has not been applied and the vector makes it possible to reduce shadows as artifacts without reducing the space resolution of the three-dimensional image data.

In a fifth aspect of the present invention, a medical image-processing apparatus comprises an image processor configured to receive image data represented by a predetermined three-dimensional coordinate system and apply a process for smoothing the vector based on the image data, thereby generating three-dimensional image data based on image data to which a smoothing process has not been applied, according to the orientation of the smoothed vector.

In a sixth aspect of the present invention, an ultrasonic image-processing method comprises the steps of: obtaining received data by transmitting ultrasonic waves to a subject to be examined and receiving reflected waves from the subject to be examined; and applying a process for smoothing the vector based on the received data to generate three-dimensional image data based on received signals that have been unaffected by the smoothing, according to the orientation of the smoothed vector.

BRIEF DESCRIPTION OF THE DRAWINGS

FIG. 2 is a view for illustrating a path through which ultrasonic waves propagate.

FIG. 3 is a schematic drawing for illustrating the tilt of the vector.

FIG. 4 is a block diagram for illustrating a smoothing process according to the conventional art.

FIG. 5 is a block diagram for illustrating a smoothing process according to the conventional art.

DETAILED DESCRIPTION OF THE EMBODIMENTS

First Embodiment

Figure 1:
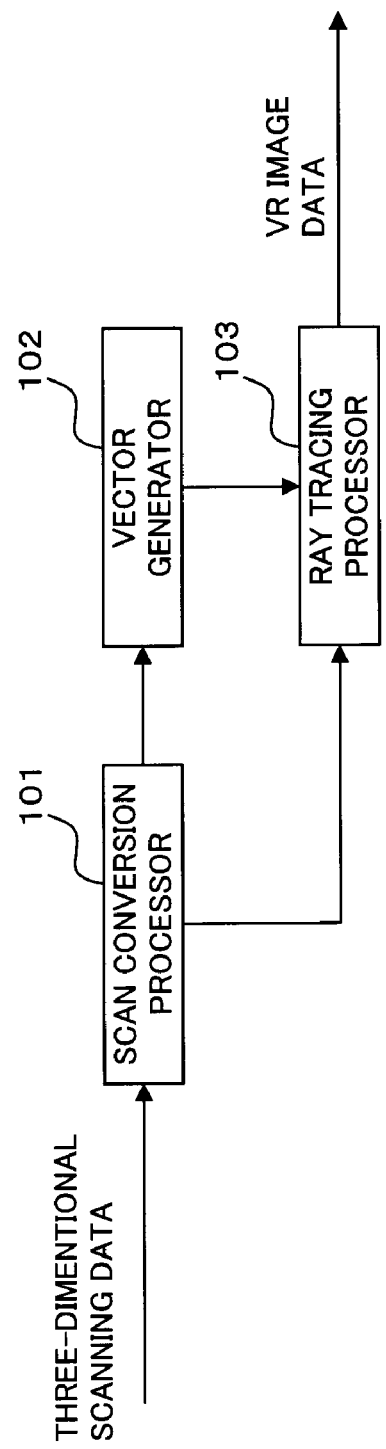
FIG. 1 is a block diagram showing a portion of an ultrasonic imaging apparatus according to a conventional art.
Figure 6:
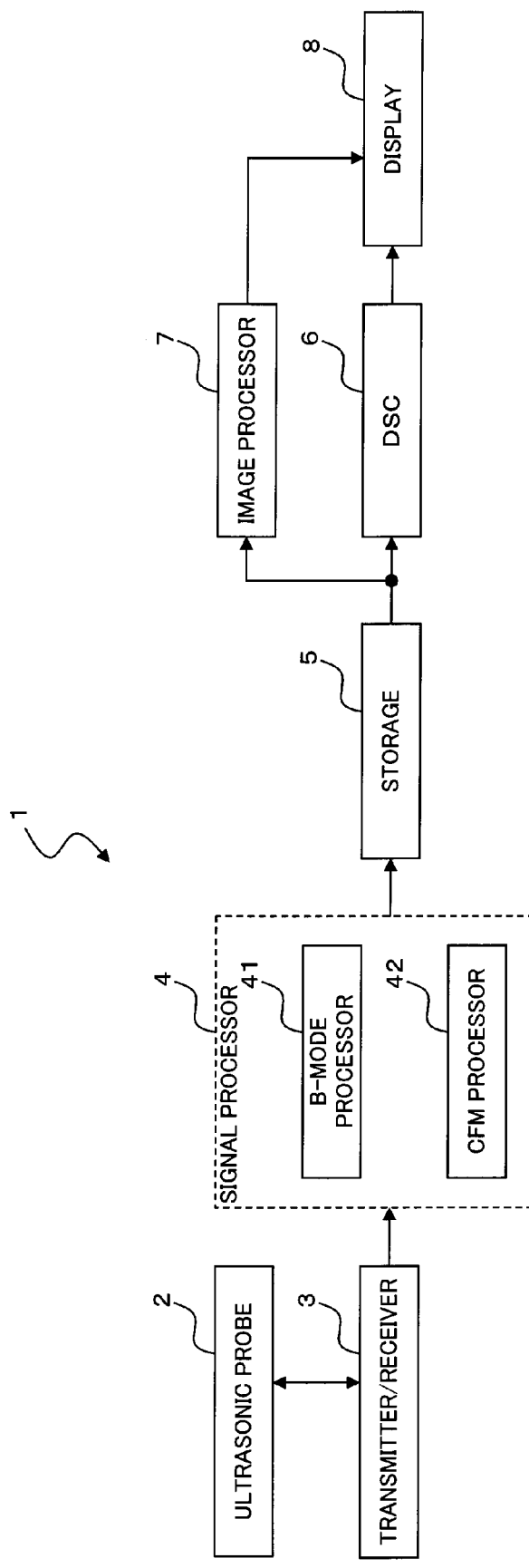
FIG. 6 is a block diagram showing an ultrasonic imaging apparatus according to a first embodiment of the present invention.

An ultrasonic imaging apparatus and an ultrasonic image-processing method according to a first embodiment of the present invention will be described referring to FIG. 6. FIG. 6 is a block diagram showing an ultrasonic imaging apparatus according to the first embodiment of the present invention.

An ultrasonic imaging apparatus 1 according to the first embodiment applies a smoothing process to three-dimensional scanning data or voxel data, and calculates the vector of each voxel by using the smoothed three-dimensional scanning data or the smoothed voxel data. Then, the ultrasonic imaging apparatus 1 generates shaded three-dimensional image data, based on the vector and voxel data to which a smoothing process has not been applied. That is, the ultrasonic imaging apparatus 1 smoothes the three-dimensional scanning data or the voxel data in order to calculate the vector, and uses, as the voxel data to be subjected to a ray-tracing process, the voxel data to which a smoothing process has not been applied. This makes it possible to reduce shadows as artifacts without reducing the space resolution of the three-dimensional image. Each part of the ultrasonic imaging apparatus 1 will be described below.

An ultrasonic probe 2 is composed of a two-dimensional array probe on which a plurality of ultrasonic transducers is two-dimensionally arranged. Then, the ultrasonic probe 2 three-dimensionally transmits and receives ultrasonic waves, and receives, as an echo signal, three-dimensional data in the form of radiating out from the probe surface.

For the ultrasonic probe 2, a one-dimensional array probe on which a plurality of ultrasonic transducers are arranged in a line in a predetermined direction (scanning direction), the one-dimensional array probe being capable of mechanically swinging the ultrasonic transducers in a direction (swing direction) perpendicular to the scanning direction may also be used instead of the two-dimensional ultrasonic probe. Thus, an ultrasonic probe capable of scanning a three-dimensional space is used in the first embodiment.

Figure 7:
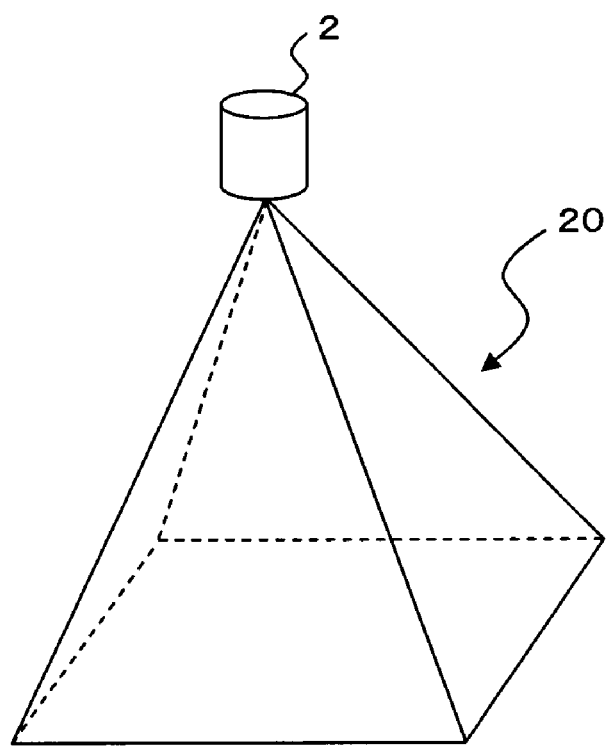
FIG. 7 is a schematic drawing for illustrating a region where an ultrasonic probe can scan.

A region where the ultrasonic probe 2 can scan will now be described referring to FIG. 7. FIG. 7 is a schematic drawing for illustrating a region where an ultrasonic probe can scan. A region 20 where the ultrasonic probe 2 can scan is a three-dimensional space. When a two-dimensional array probe is used as the ultrasonic probe 2, the ultrasonic probe 2 scans the three-dimensional space by electronically scanning ultrasonic waves. When a one-dimensional array probe is used as the ultrasonic probe 2, the ultrasonic probe 2 scans the three-dimensional space by mechanically swinging ultrasonic transducers.

A transmitter/receiver 3 is provided with a transmitter and a receiver. The transmitter/receiver 3 generates ultrasonic waves by supplying electrical signals to the ultrasonic probe 2 under the control of a controller not shown herein. Further, the transmitter/receiver 3 receives echo signals that the ultrasonic probe 2 has received. The data output from the transmitter/receiver 3 is output to a signal processor 4.

The specific configuration of the transmitter will now be described. The transmitter is provided with a clock generation circuit, a transmission delay circuit and a pulsar circuit, which are not shown herein. The clock generation circuit generates clock signals to determine the transmission timing or the transmission frequency of the ultrasonic wave signal. The transmission delay circuit performs transmission focus by applying a delay at the time of transmission of ultrasonic waves. The pulsar circuit houses a pulsar in a number of individual channels corresponding to the respective ultrasonic transducers. The pulsar circuit generates a driving pulse at the delayed transmission timing and supplies to the respective ultrasonic transducers of the ultrasonic probe 2.

The receiver is provided with a preamplifier circuit, an A/D conversion circuit and a reception delay/adder circuit, which are not shown herein. The preamplifier circuit amplifies echo signals output from the respective ultrasonic transducers of the ultrasonic probe 2 for the respective reception channels. The A/D conversion circuit provides A/D conversion of the amplified echo signals. The reception delay/adder circuit performs addition by providing a delay time required to determine the receiving directivity to the echo signals after the A/D conversion. With this addition, the reflected component from a direction according to the receiving directivity is emphasized. The signals to which the addition process has been applied by the transmitter/receiver 3 are referred to as "RF signals." These RF signals are output from the transmitter/receiver 3 to the signal processor 4.

A B-mode processor 41 converts amplitude information of the echo to an image, and generates B-mode ultrasonic raster data (hereinafter, ma be referred to as "scanning data") from the echo signals. Specifically, the B-mode processor 41 executes a Band Pass Filter process on the data (RF signals) output from the transmitter/receiver 3. Then, the B-mode processor 41 detects the envelope curve of the output signals, and applies a compression process to the detected data by means of logarithmic conversion. The data generated by the B-mode processor 41 is referred to as B-mode ultrasonic raster data. This B-mode ultrasonic raster data is equivalent to one example of the "scanning data" of the present invention. In addition, the ultrasonic probe 2, the transmitter/receiver 3, and the signal processor 4 are equivalent to one example of the "scanner" of the present invention.

A CFM processor 42 converts information on a moving bloodstream to an image, and generates color ultrasonic raster data.

A storage 5 temporarily stores the ultrasonic raster data (scanning data) generated by the signal processor 4.

A DSC (Digital Scan Converter) 6 converts the ultrasonic raster data obtained two-dimensionally (hereinafter, may be referred to as "two-dimensional scanning data") into image data represented by Cartesian coordinates, in order to obtain an image represented by the Cartesian coordinate system (scan conversion process). For example, in the case of scanning of a two dimensional cross-section by the ultrasonic probe 2, the DSC 6 reads out the ultrasonic raster data (two-dimensional scanning data) from the storage 5, and applies a two-dimensional scan conversion process to the ultrasonic raster data, thereby generating two-dimensional image data. The two-dimensional image data is output to a display 8, and the display 8 displays a two-dimensional image based on the two-dimensional image data. For example, the DSC 6 generates tomographic image data as two-dimensional information, based on the B-mode ultrasonic raster data, and outputs the tomographic image data to the display 8. The display 8 displays a tomographic image based on the tomographic image data.

An image processor 7 performs a three-dimensional scan conversion process on the ultrasonic raster data obtained three-dimensionally (hereinafter, may be referred to as "three-dimensional scanning data"), thereby generating voxel data. Furthermore, the image processor 7 applies image processing such as a volume rendering process or a MPR process to the voxel data, thereby generating image data such as three-dimensional image data or MPR image data.

Figure 8:
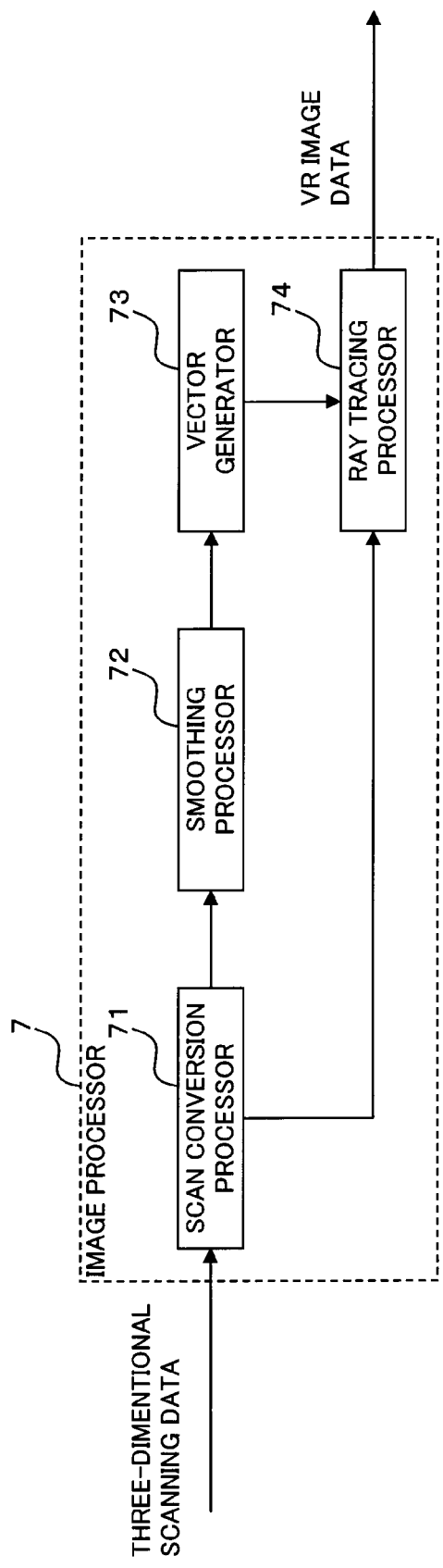
FIG. 8 is a block diagram showing an image processor according to the first embodiment of the present invention.

The configuration of the image processor 7 will be described referring to FIG. 8. FIG. 8 is a block diagram showing an image processor according to the first embodiment of the present invention.

Figure 9:
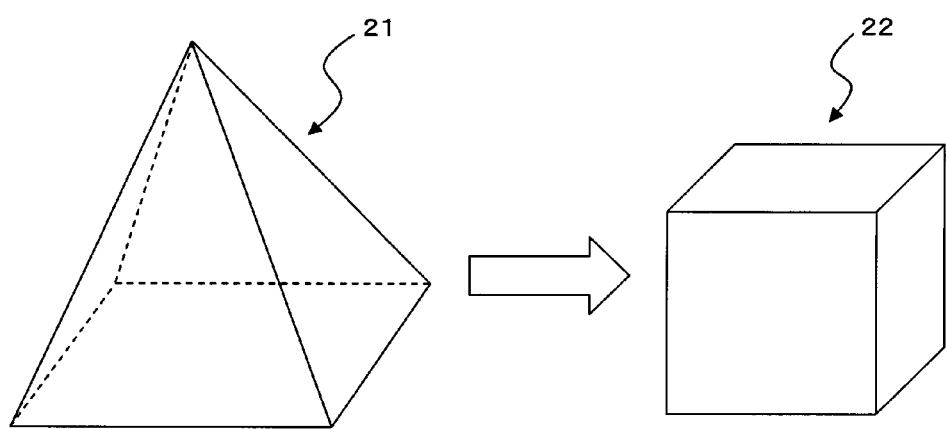
FIG. 9 is a schematic drawing showing ultrasonic raster data (three-dimensional scanning data) and voxel data.

A scan conversion processor 71 reads out the ultrasonic raster data obtained three-dimensionally (three-dimensional scanning data) from the storage 5, and applies a three-dimensional scan conversion process to the three-dimensional scanning data, thereby generating voxel data represented by the Cartesian coordinate system. The three-dimensional scan conversion process will now be described referring to FIG. 9. FIG. 9 is a schematic drawing showing ultrasonic raster data (three-dimensional scanning data) and voxel data. The scan conversion processor 71 reads out ultrasonic raster data (three-dimensional scanning data) 21 from the storage 5, and applies a three-dimensional scan conversion process to the ultrasonic raster data 21, thereby generating voxel data 22 represented by the Cartesian coordinate system. Then, the scan conversion processor 71 outputs the voxel data to a smoothing processor 72 and a ray-tracing processor 74. The scan conversion processor 71 is equivalent to one example of the "converter" of the present invention.

As described above, the scan conversion processor 71 converts three-dimensional scanning data into voxel data represented by the Cartesian coordinate system in the first embodiment. Thus, the scan conversion processor 71 converts three-dimensional scanning data to image data represented by a preset specified three-dimensional coordinate system. The conversion process to voxel data is one example of the conversion process of the present invention. The scan conversion processor 71 may also convert three-dimensional scanning data into image data represented by a three-dimensional coordinate system other than the Cartesian coordinate system. A case in which the scan conversion processor 71 generates voxel data represented by the Cartesian coordinate system will be described below.

Upon receiving voxel data from the scan conversion processor 71, a smoothing processor 72 applies a smoothing process to the voxel data by using a predetermined smoothing filter. The smoothing processor 72 calculates, for example, an average of voxel data within a preset specified range. Then, the smoothing processor 72 outputs the voxel data after the smoothing process to a vector generator 73. This voxel data after the smoothing process is used to calculate the vector. When the scan conversion processor 71 generates image data represented by a three-dimensional coordinate system other than the Cartesian coordinate system, the smoothing processor 72 applies a smoothing process to the image data.

Upon receiving the voxel data after the smoothing process from the smoothing processor 72, the vector generator 73 obtains the vector of each voxel. For example, the vector generator 73, for a certain voxel and voxels surrounding the voxel, obtains differentiation of the voxel values to obtain a tangent line of the voxel. Then, the vector generator 73 defines a vector perpendicular to the tangent line as the vector. Next, the vector generator 73 finds the vector of each voxel. At this time, the vector generator 73 normalizes the vector to convert the same into a unit vector. The "vector" will be described hereinafter as indicating the "unit vector." Thereafter, the vector generator 73 outputs the vector of each voxel to a ray tracer 74. When the scan conversion processor 71 generates image data represented by a three-dimensional coordinate system other than the Cartesian coordinate system, the vector generator 73 finds the vector of each point, based on the image data after the smoothing process.

Figure 10:
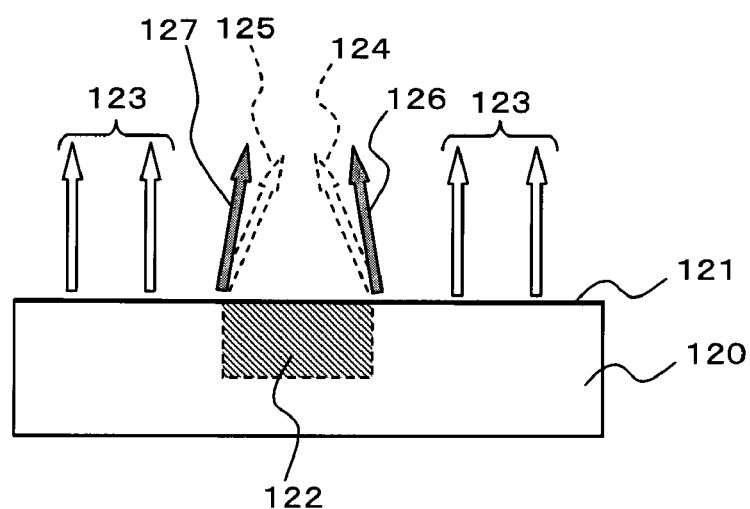
FIG. 10 is a schematic drawing for illustrating the tilt of the vector before and after the smoothing process.

As described above, finding the vector of each voxel based on the voxel data after the smoothing process makes it possible to prevent the vector from abruptly changing. The tilt of the vector before and after the smoothing process will now be described referring to FIG. 10. FIG. 10 is a schematic drawing for illustrating the tilt of the vector before and after the smoothing process.

As shown in FIG. 10, for example, when three-dimensional scanning data of a certain tissue 120 is obtained, if a site 122 where the value of the three-dimensional scanning data changes abruptly exists on a surface 121 of the tissue 120, the orientations of vectors 124 and 125 of the surface 121 on which the site 122 exists will significantly tilt with reference to the orientation of a vector 123 of another site. If there is no concavity and convexity on the surface 121, the orientation of the vector does not significantly tilt spatially. However, because there is a location where the value of the three-dimensional scanning data changes abruptly, the tilt of the vector at that location will be significant.

On the other hand, the smoothing processor 72 applies a smoothing process to voxel data in the first embodiment. Then, the vector generator 73 finds the vector, based on the voxel data after the smoothing process. This makes it possible to prevent the vector from abruptly changing. Consequently, as shown in FIG. 10, the vector 124 before the smoothing process is converted into a vector 126 with a gradual tilt by a smoothing process. Similarly, the vector 125 before the smoothing process is applied is converted into a vector 127 with a gradual tilt by a smoothing process. This makes it possible to prevent the vector from abruptly changing on the surface of spatially contiguous tissues, even if there is a location where a voxel value abruptly changes.

Figure 11:
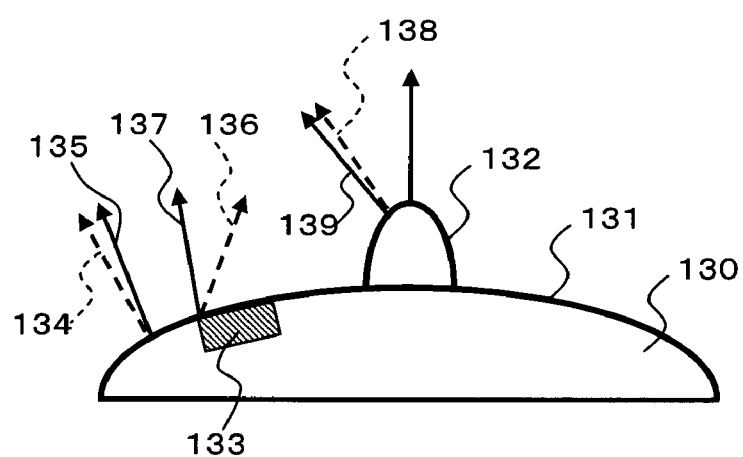
FIG. 11 is a schematic drawing for illustrating the tilt of the vector before and after the smoothing process and a sectional view of the surface of a subject to be examined.

In addition, according to the first embodiment, it becomes possible to effectively prevent fluctuations of the vector causing a shadow as an artifact while maintaining the orientation of the vector in a structure (such as the edge of a nose) supposed to be shaded originally. This action will be described referring to FIG. 11. FIG. 11 is a schematic drawing for illustrating the tilt of the vector before and after the smoothing process and a sectional view of the face of a subject to be examined.

As shown in FIG. 11, for example, when three-dimensional scanning data of a face 130 is obtained, if a site 133 exists where the value of the three-dimensional scanning data changes abruptly, the orientation of a vector 136 of a surface 131 on which the site 133 exists will significantly tilt with reference to the vector 134 of another site. According to the first embodiment, the smoothing processor 72 applies a smoothing process to voxel data. Then, the vector generator 73 finds the vector, based on the voxel data after the smoothing process. This makes it possible to prevent the vector from abruptly changing. Consequently, as shown in FIG. 11, the vector 136 before the smoothing process is converted into a vector 137 with a gradual tilt by the smoothing process. In other words, it becomes possible to prevent the vector from abruptly changing on the surface of spatially contiguous tissues, even if there exists a location where a voxel value abruptly change.

On the other hand, in a structure (such as the edge of a nose 132) that is supposed to be shaded, it is possible to maintain the orientation of the vector even when applying the smoothing process. For example, a vector 138 on the edge of the nose 132 is converted into a vector 139 by the smoothing process. However, a tilt thereof changes slightly at most, and the original tilt is maintained. In addition, the vector 134 of the surface 131 of the face 130 is also converted into a vector 135 by the smoothing process. However, a tilt thereof changes slightly at most, and the original tilt is maintained.

As described above, according to the ultrasonic imaging apparatus in accordance with the first embodiment, the orientation of the vector can be maintained in a structure supposed to be shaded originally. Furthermore, according to the ultrasonic imaging apparatus in accordance with the first embodiment, it becomes possible to effectively prevent the tilt of the vector causing a shadow that should be removed.

Upon receiving voxel data from the scan conversion processor 71 and furthermore receiving the vector of each voxel from the vector generator 73, the ray-tracing processor 74 generates three-dimensional image data by applying a ray-tracing process to the voxel data. The voxel data output from the scan conversion processor 71 has not been subjected to a smoothing process. On the other hand, the vector output from the vector generator 73 is found, based on the voxel data to which a smoothing process has been applied. The ray-tracing processor 74 generates shaded three-dimensional image data by applying a ray-tracing process to the voxel data to which a smoothing process has not been applied, according to the vector obtained based on the voxel data to which a smoothing process has been applied. The ray-tracing processor 74 finds the luminance (reflection brightness) at a certain point on an object surface, based on the direction of a ray from a light source set by the ray-tracing process and the orientation of the vector calculated by the vector generator 73, thereby generating a shaded three-dimensional image data. Specifically, the ray-tracing processor 74 shades by using a vector indicating the direction of the ray from the light source and the vector, based on the Phong model that is a representative shading model. A model other than the Phong model may also be used. The ray-tracing processor 74 is equivalent to one example of the "three-dimensional image generator" of the present invention. In addition, when the scan conversion processor 71 generates image data represented by a three-dimensional coordinate system other than the Cartesian coordinate system, the ray-tracing processor 74 generates three-dimensional image data by applying a ray-tracing process to the image data.

As described above, voxel data subjected to a process by the ray-tracing processor 74 is not subjected to a smoothing process. Therefore, generating three-dimensional image data based on the voxel data makes it possible to generate three-dimensional image data without reducing the space resolution.

Then, the image processor 7 outputs shaded three-dimensional image data to the display 8. Consequently, a three-dimensional image based on the shaded three-dimensional image data is displayed on the display 8.

As described above, according to the ultrasonic imaging apparatus in accordance with the first embodiment, because voxel data to which a smoothing process has not been applied is used as voxel data to be subjected to a ray-tracing process, reduction of the space resolution of three-dimensional image data is avoided. Furthermore, using voxel data after the smoothing process as voxel data for finding the vector of the voxel makes it possible to reduce shadows as artifacts.

The image processor 7 is composed of an ASIC (application-specific integrated circuit), an FPGA (field programmable gate array), or a CPU (central processing unit) housed in the ultrasonic imaging apparatus 1. In addition, the image processor 7 may also be composed of a workstation or the like installed outside the ultrasonic imaging apparatus 1. For example, an image-processing program for performing the functions of the image processor 7 is prestored on a storage device such as ROM (read-only memory), RAM (random access memory), or an HDD (hard disk drive). This image-processing program includes a scan conversion process program for performing the functions of the scan conversion processor 71, a smoothing process program for performing the functions of the smoothing processor 72, a vector calculation program for performing the functions of the vector generator 73, and a ray-tracing process program for performing the functions of the ray-tracing processor 74. The CPU applies a scan conversion process to three-dimensional scanning data by executing the scan conversion process program. The CPU performs a smoothing process on voxel data by executing the smoothing process program. The CPU finds the vector by executing the vector calculation program. In addition, the CPU applies a ray-tracing process to voxel data to generate three-dimensional image data by executing the ray-tracing process program.

The display 8 is composed of a monitor such as a CRT or an LCD (liquid crystal display). The display 8 displays an image such as a tomographic image, a three-dimensional image, or bloodstream information on a monitor screen.

In addition, the ultrasonic imaging apparatus 1 is provided with a controller not shown herein. The controller is connected to each part of the ultrasonic imaging apparatus 1 and controls the operations of each part of the ultrasonic imaging apparatus 1. Moreover, the ultrasonic imaging apparatus 1 is provided with an operating part (not shown) for inputting various settings regarding the transmitting/receiving conditions of ultrasonic waves. This operating part is composed of a pointing device such as a joystick or a trackball, a switch, various buttons, a keyboard, or a TCS (Touch Command Screen).

Modification 1

Figure 12:
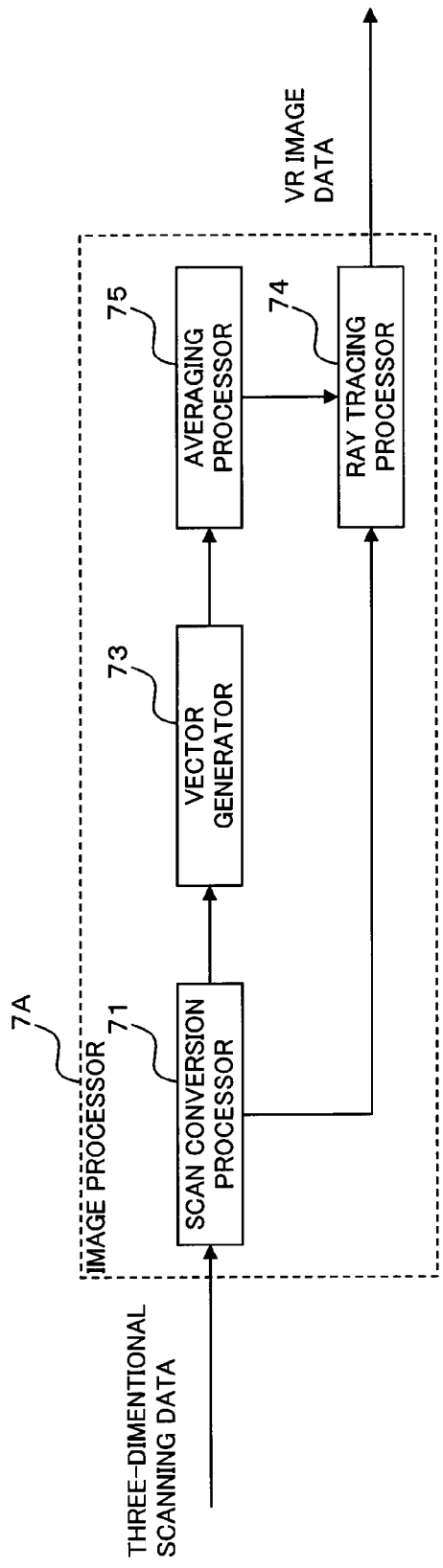
FIG. 12 is a block diagram showing an image processor according to a modification 1.

Next, a modification 1 of the first embodiment will be described referring to FIG. 12. FIG. 12 is a block diagram showing an image processor according to the modification 1.

The configuration of the image processor is changed in the modification 1. An ultrasonic imaging apparatus according to the modification 1 comprises an image processor 7A instead of the image processor 7 described above. In addition, regarding the configuration other than that of the image processor, the ultrasonic imaging apparatus according to the modification 1 comprises the same configuration as that of the ultrasonic imaging apparatus according to the first embodiment. The configuration of the image processor 7A will be described below, but explanation of the configuration other than that of the image processor 7A will be omitted.

The image processor 7A according to the modification 1 comprises an averaging processor 75 instead of the averaging processor 72 that the image processor 7 comprises. In addition, the scan conversion processor 71, vector generator 73 and ray-tracing processor 74 that image processor 7A comprises perform the same processes as the image processor 7 according to the first embodiment.

Upon receiving the vector found by the vector generator 73, the averaging processor 75 calculates, for a plurality of vectors included within a preset specified range, an average of the vectors. The averaging processor 75 averages the vectors of the respective voxels by this process. Then, the averaging processor 75 outputs the averaged vector to the ray-tracing processor 74.

As described above, averaging the vectors makes it possible to prevent the vectors from abruptly changing. This makes it possible to prevent the vector from abruptly changing on the surface of spatially contiguous tissues, even if there exists a location where a voxel value abruptly changes.

Upon receiving voxel data from the scan conversion processor 71 and furthermore receiving the vector of each voxel from the averaging processor 75, the ray-tracing processor 74 generates three-dimensional image data by applying a ray-tracing process to the voxel data. In the modification 1, the voxel data output from the scan conversion processor 71 to the ray-tracing processor 74 is not subjected to an averaging process. On the other hand, the vector output from the averaging processor 75 to the ray-tracing processor 74 is averaged by the averaging processor 75. Then, the ray-tracing processor 74 generates shaded three-dimensional image data by applying a ray-tracing process to the voxel data to which an averaging process has not been applied, according to the averaged vector.

As described above, voxel data subjected to the process by the ray-tracing processor 74 is not subjected to an averaging process. Therefore, generating three-dimensional image data based on the voxel data makes it possible to generate three-dimensional image data without reducing the space resolution.

The image processor 7A outputs shaded three-dimensional image data to the display 8. Consequently, a three-dimensional image based on the shaded three-dimensional image data is displayed on the display 8.

As described above, according to the ultrasonic imaging apparatus in accordance with the modification 1, voxel data to which an averaging process has not been applied is use as voxel data to be subjected to a ray-tracing process. In addition, the averaged vector is used for a ray-tracing process. This enables a reduction of shadows as artifacts without reducing the space resolution of three-dimensional image data.

The scan conversion processor 71 may generate image data represented by a three-dimensional coordinate system other than the Cartesian coordinate system also in modification 1. In this case, the vector is found based on the image data, and furthermore three-dimensional image data is generated based on the image data.

Modification 2

Figure 13:
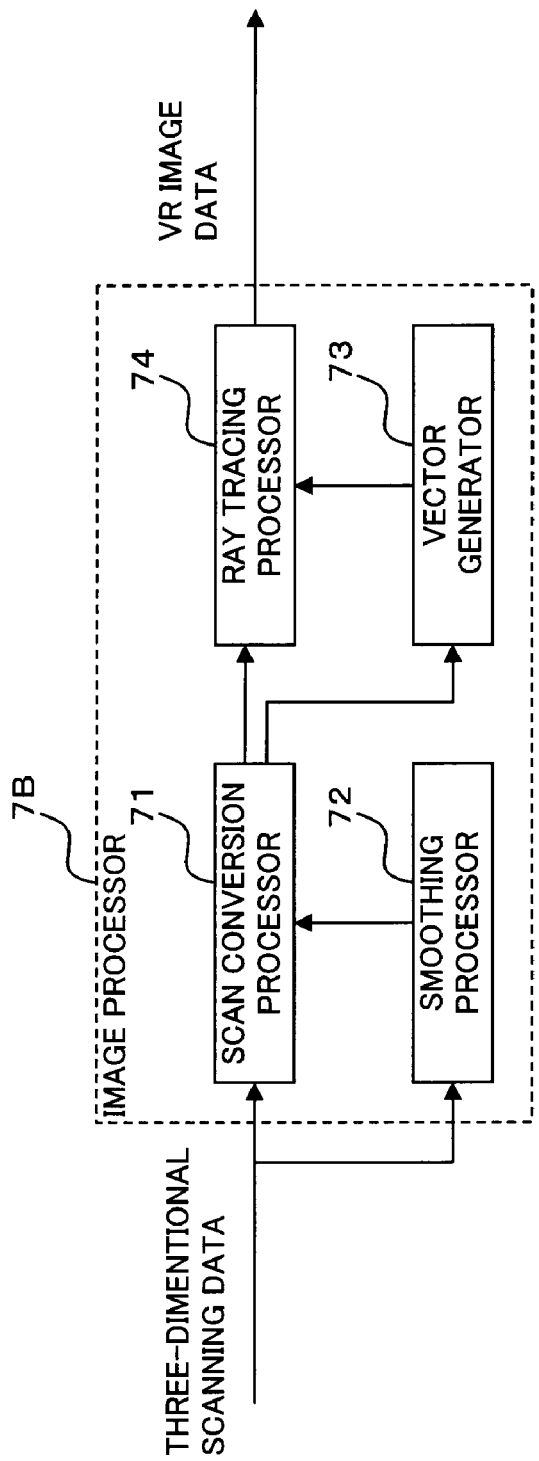
FIG. 13 is a block diagram showing an image processor according to a modification 2.

Next, a modification 2 of the first embodiment will be described referring to FIG. 13. FIG. 13 is a block diagram showing an image processor according to the modification 2.

The configuration of the image processor is changed in modification 2. An ultrasonic imaging apparatus according to modification 2 comprises an image processor 7B instead of the image processor 7. In addition, regarding the configuration other than that of the image processor, the ultrasonic imaging apparatus according to the modification 2 comprises the same configuration as that of the ultrasonic imaging apparatus 1 according to the first embodiment. The configuration of the image processor 7B will be described below, but explanation of the configuration other than that of the image processor 7B will be omitted.

The image processor 7B according to the modification 2 comprises, as well as the image processor 7 according to the first embodiment, the scan conversion processor 71, the smoothing processor 72, the vector generator 73, and the ray-tracing processor 74. In the first embodiment, smoothing is performed on the data after scan conversion. On the other hand, in the modification 2, smoothing is performed on the data (scanning data) before scan conversion. The configuration of the image processor 7B is the same as the configuration of the image processor 7 according to the first embodiment. However, a process flow in the image processor 7B is different from that in the imaging processor 7.

The scan conversion processor 71 reads out ultrasonic raster data (three-dimensional scanning data) from the storage 5, and applies a three-dimensional scan conversion process to the three-dimensional scanning data, thereby generating voxel data. The scan conversion processor 71 outputs the voxel data to the ray-tracing processor 74. This voxel data is subjected to a ray-tracing process by the ray-tracing processor 74. As described above, voxel data to which a smoothing process has not been applied in the generation process thereof is used as voxel data subjected to the ray-tracing process. The voxel data to which a smoothing process has not been applied in the generation process will be referred to as "first voxel data" for descriptive purposes.

The smoothing processor 72 reads out three-dimensional scanning data from the storage 5, and applies a smoothing process to the three-dimensional scanning data by using a preset specified smoothing filter. Then, the smoothing processor 72 outputs the three-dimensional scanning data after the smoothing process to the scan conversion processor 71. Upon receiving the three-dimensional scanning data after the smoothing process from the smoothing processor 72, the scan conversion processor 71 generates voxel data by applying a three-dimensional scan conversion process to the three-dimensional image data after the smoothing process. Thus, the voxel data has been subjected to a smoothing process in the generation process thereof. The scan conversion processor 71 outputs the voxel data to which the smoothing process has been applied in the generation process, to the vector generator 73. Thus, the voxel data to which the smoothing process has been applied in the generation process thereof is used as voxel data to be used in calculation of the vector. The voxel data to which the smoothing process has been applied in the generation process will be referred to as "second voxel data" for descriptive purposes.

Upon receiving the second voxel data (voxel data to which a smoothing process has been applied in the generation process) from the scan conversion processor 71, the vector processor 73 finds the vector of each voxel. The second voxel data has been subjected to a smoothing process in the generation process thereof, so that it becomes possible to prevent the vector from abruptly changing. This makes it possible to prevent the vector from abruptly changing on the surface of spatially contiguous tissues, even if there exists a location where a voxel value abruptly changes.

Upon receiving the first voxel data (voxel data to which a smoothing process has not been applied) from the scan conversion processor 71 and furthermore receiving the vector found based on the second voxel data (voxel data to which a smoothing process has been applied in the generation process) from the vector generator 73, the ray-tracing processor 74 generates shaded three-dimensional image data by applying a ray-tracing process to the first voxel data.

As described above, voxel data subjected to the process by the ray-tracing processor 74 (first voxel data) has not been subjected to a smoothing process. Therefore, generating three-dimensional image data based on the voxel data makes it possible to generate three-dimensional image data without reducing the space resolution.

The image processor 7B outputs shaded three-dimensional image data to the display 8. Consequently, a three-dimensional image based on the shaded three-dimensional image data is displayed on the display 8.

As described above, according to the ultrasonic imaging apparatus in accordance with the modification 2, voxel data to which a smoothing process has not been applied is used as voxel data to be subjected to a ray-tracing process. In addition, voxel data to which a smoothing process has been applied in the generation process thereof is used as voxel data for finding the vector of the voxel. This enables a reduction of shadows as artifacts without reducing the space resolution of three-dimensional image data.

The scan conversion processor 71 may generate image data represented by a three-dimensional coordinate system other than the Cartesian coordinate system also in the modification 2.

Modification 3

Figure 14:
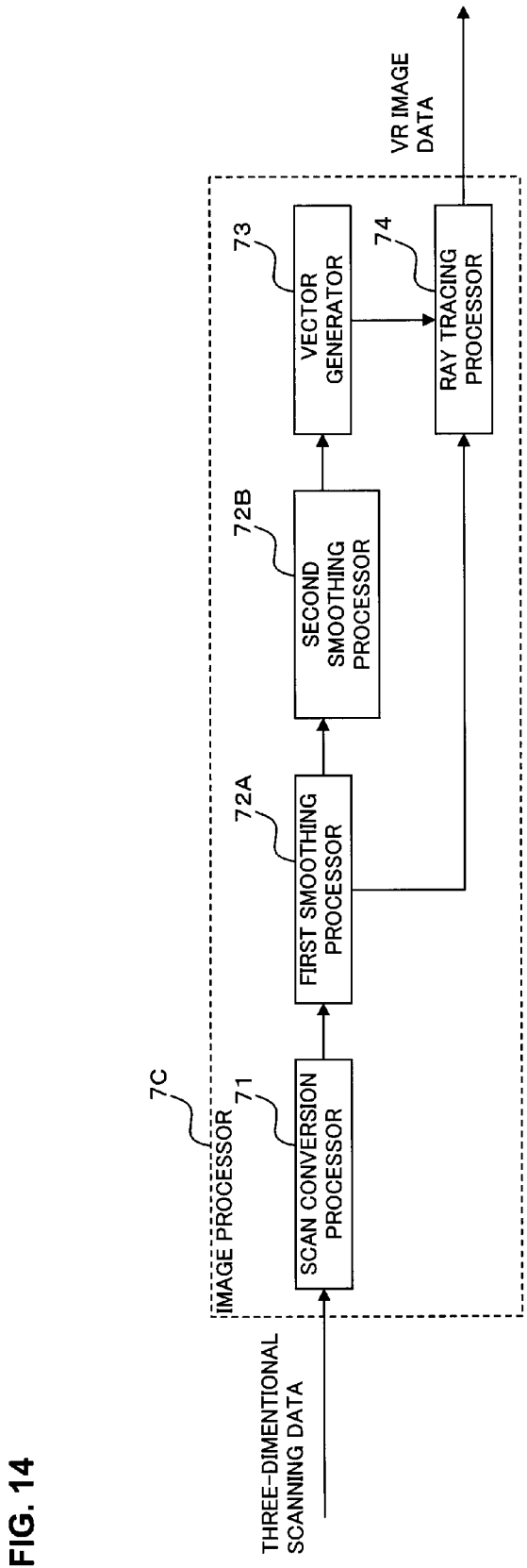
FIG. 14 is a block diagram showing an image processor according to a modification 3.

Next, a modification 3 of the first embodiment will be described referring to FIG. 14. FIG. 14 is a block diagram showing an image processor according to the modification 3.

In the first embodiment, the modification 1 and the modification 2 described above, a smoothing process is not applied to voxel data subjected to a ray-tracing process. A smoothing process may be applied to the voxel data subjected to a ray-tracing process by using a weak smoothing filter for simply removing noise. For example, an image processor 7C according to the modification 3 comprises a first smoothing processor 72A and a second smoothing processor 72B.

The first smoothing processor 72A applies a first smoothing process to voxel data generated by the scan conversion processor 71. As a first smoothing filter used in this first smoothing process, a weak filter for simply removing noise from the voxel data is used. Then, the first smoothing processor 72A outputs the voxel data to which the first smoothing process has been applied, to the second smoothing processor 72B and the ray-tracing processor 74.

The second smoothing processor 72B applies a second smoothing process to the voxel data to which the first smoothing process has been applied. Then, the second smoothing processor 72B outputs the voxel data to which the second smoothing process has been applied, to the vector generator 73. As a second smoothing filter used in this second smoothing process, the same smoothing filter as the first smoothing filter used in the first smoothing process may be used. In addition, a smoothing filter having a stronger smoothing action than the first smoothing filter may also be used as the second smoothing filter. For example, making a range in which the smoothing process is performed broader than that of the first smoothing filter can strengthen the smoothing action.

The vector generator 73 finds the vector of each voxel, based on the voxel data to which the second smoothing process has been applied. Thus, finding the vector of each voxel based on the voxel data to which the first and second smoothing processes have been applied makes it possible to prevent the vector from abruptly changing. That is, it becomes possible to prevent the vector from abruptly changing on the surface of spatially contiguous tissues, even if there exists a location where a voxel value abruptly changes.

Upon receiving the voxel data to which the first smoothing process has been applied from the first smoothing processor 72A, and furthermore receiving the vector of each voxel from the vector generator 73, the ray-tracing processor 74 generates three-dimensional image data by applying a ray-tracing process to the voxel data. Since the first smoothing filter used in the first smoothing processor 72A is a weak filter for simply removing noise, the reduction of space resolution of three-dimensional image data is avoided. In addition, for the vector found based on the voxel data to which the first and second smoothing processes have been applied, it is prevented from abruptly changing, whereby it becomes possible to remove shadows as artifacts.

The image processor 7C outputs shaded three-dimensional image data to the display 8. Consequently, a three-dimensional image based on the shaded three-dimensional image data is displayed on the display 8.

The ultrasonic imaging apparatus according to the modification 3 applies the first smoothing process to the voxel data after a scan conversion process. Instead of this process, the first smoothing process may also be applied to three-dimensional scanning data before the scan conversion process. In addition, the first smoothing process using a weak smoothing filter for simply removing noise may be performed also in the modification 1 and the modification 2. For example, in the modification 1, the first smoothing process may also be performed to voxel data after the scan conversion process. In addition, the first smoothing process may also be performed on three-dimensional scanning data before the scan conversion process. In the modification 2, the first smoothing process may also be performed on three-dimensional scanning data before the scan conversion process. Moreover, the first smoothing process may also be preformed on voxel data to be output to the ray-tracing processor 74.

As described above, even if a weak smoothing filter for simply removing noise is made to act on three-dimensional scanning data or voxel data, the action of the smoothing filter is weak, whereby the reduction of space resolution of three-dimensional image data is avoided. Then, using voxel data to which the first and second smoothing processes have been applied as voxel data used in calculation of the vector makes it possible to prevent the vector from abruptly changing. That makes it possible to remove shadows as artifacts.

The scan conversion processor 71 may generate image data represented by a three-dimensional coordinate system other than the Cartesian coordinate system also in the modification 3.

Second Embodiment

Figure 15:
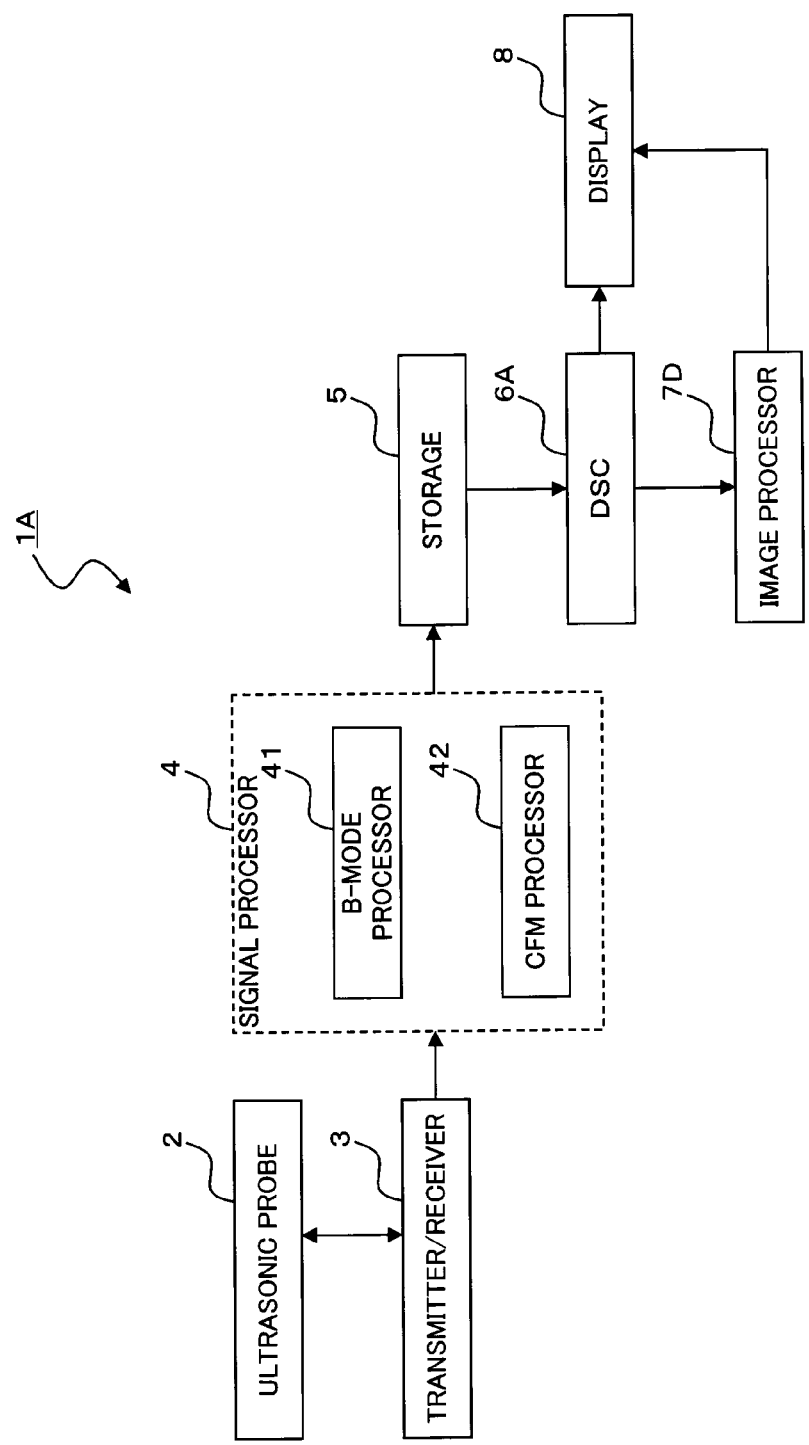
FIG. 15 is a block diagram showing an ultrasonic imaging apparatus according to a second embodiment of the present invention.

Next, an ultrasonic imaging apparatus and an ultrasonic image-processing method according to the second embodiment of the present invention will be described referring to FIG. 15. FIG. 15 is a block diagram showing an ultrasonic imaging apparatus according to the second embodiment of the present invention.

The configuration of the DSC and the image processor is changed in the second embodiment. An ultrasonic imaging apparatus 1A according to the second embodiment comprises a DSC 6A instead of the DSC 6, and further comprises an image processor 7D instead of the image processor 7. In the ultrasonic imaging apparatus 1A according to the second embodiment, the DSC 6A performs a scan conversion process and smoothing process, and the image processor 7C performs calculation of the vector and a ray-tracing process.

Regarding the configuration other than that of the DSC 6A and the image processor 7D, the ultrasonic image processor 1A according to the second embodiment comprises the same configuration as the ultrasonic imaging apparatus 1 according to the first embodiment. The configuration of the DSC 6A and the image processor 7D will be described below, but explanation of the configuration other than that of the DSC 6A and the image processor 7D will be omitted.

Figure 16:
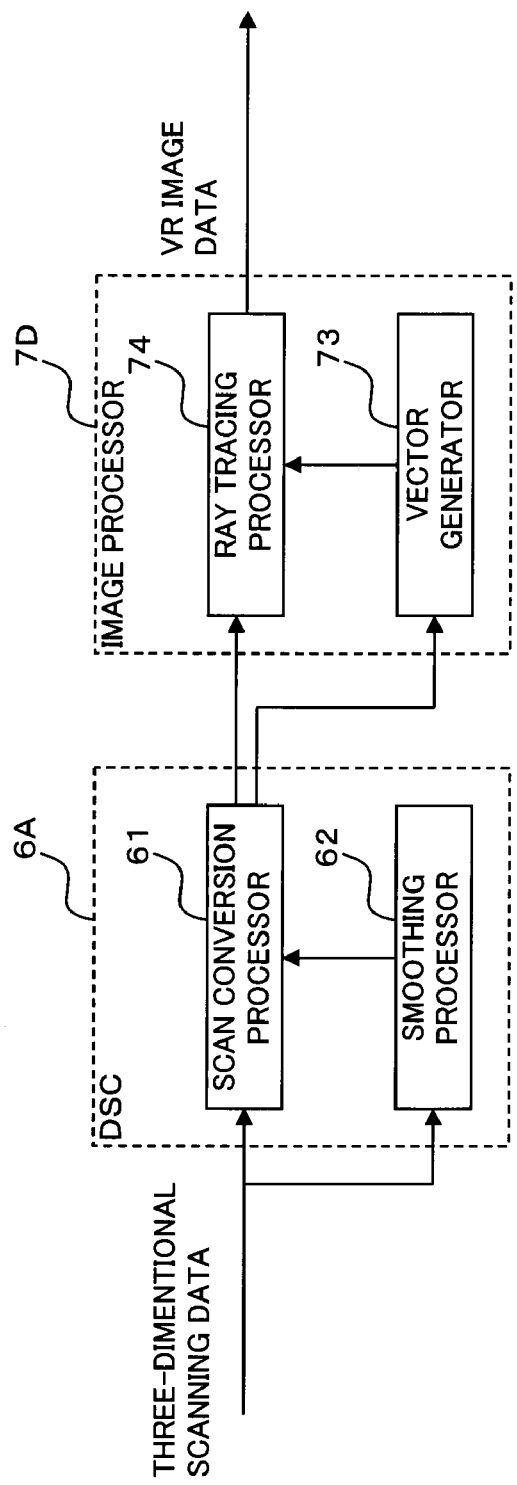
FIG. 16 is a block diagram showing the DSC and the image processor according to the second embodiment of the present invention.

The configuration of the DSC 6A and the image processor 7D is shown in FIG. 16. FIG. 16 is a block diagram showing the DSC and the image processor according to the second embodiment of the present invention. The DSC 6A comprises a scan conversion processor 61 and a smoothing processor 62. In addition, the image processor 7D comprises the vector generator 73 and the ray-tracing processor 74.

The scan conversion processor 61 performs the same process as the scan conversion processor 71 according to the modification 3 described above. That is, the scan conversion processor 61 reads out ultrasonic raster data (three-dimensional scanning data) from the storage 5, and applies a three-dimensional scan conversion process to the three-dimensional image data, thereby generating voxel data (first voxel data). Then, the scan conversion processor 61 outputs the first voxel data to the ray-tracing processor 74 of the image processor 7D. The first voxel data is subjected to a ray-tracing process by the ray-tracing processor 74. As described above, voxel data to which a smoothing process has not been applied in the generation process thereof is used as voxel data subjected to the ray-tracing process.

The smoothing processor 62 performs the same process as the smoothing processor 72 of the modification 3 described above. That is, the smoothing processor 62 reads out three-dimensional scanning data from the storage 5, and applies a smoothing process to the three-dimensional scanning data by using a preset specified smoothing filter. Then, the smoothing processor 62 outputs the three-dimensional scanning data after the smoothing process to the scan conversion processor 61. Upon receiving the three-dimensional scanning data after the smoothing process from the smoothing processor 62, the scan conversion processor 61 generates voxel data (second voxel data) by applying a three-dimensional scan conversion process to the three-dimensional image data after the smoothing process. Thus the second voxel data has been subjected to a smoothing process in the generation process thereof. Then, the scan conversion processor 61 outputs the second voxel data to the vector generator 73 of the image processor 7D. Thus, the voxel data to which the smoothing process has been applied in the generation process thereof is used as voxel data used in calculation of the vector.

Upon receiving the second voxel data from the scan conversion processor 61 of the DSC 6A, the vector generator 73 of the image processor 7D finds the vector of each voxel. Since the second voxel data has been subjected to a smoothing process in the generation process thereof, it becomes possible to prevent the vector from abruptly changing. Consequently, it becomes possible to prevent the vector from abruptly changing on the surface of spatially contiguous tissues, even if there exists a location where a voxel value abruptly changes.

Upon receiving the first voxel data from the scan conversion processor 61 of the DSC 6A and furthermore receiving the vector found based on the second voxel data from the vector generator 73, the ray-tracing processor 74 of the image processor 7D generates shaded three-dimensional image data by applying a ray-tracing process to the first voxel data.

The image processor 7D outputs the shaded three-dimensional image data to the display 8. Consequently, a three-dimensional image based on the shaded three-dimensional image data is displayed on the display 8.

As described above, in the ultrasonic imaging apparatus 1A according to the second embodiment, voxel data to which a smoothing process has not been applied is used as voxel data to be subjected to a ray-tracing process. In addition, voxel data to which a smoothing process has been applied in the generation process thereof is used as voxel data for finding the vector of the voxel. This makes it possible to reduce shadows as artifacts without reducing the space resolution of three-dimensional image data.

In addition, also in the second embodiment, as in the modification 3 described above, a smoothing process using a weak smoothing filter for simply removing noise may be performed on voxel data to be subjected to the ray-tracing process.

Moreover, also in the second embodiment, as in the first embodiment, image data represented by a three-dimensional coordinate system other than the Cartesian coordinate system may be generated instead of voxel data.

Third Embodiment

Figure 17:
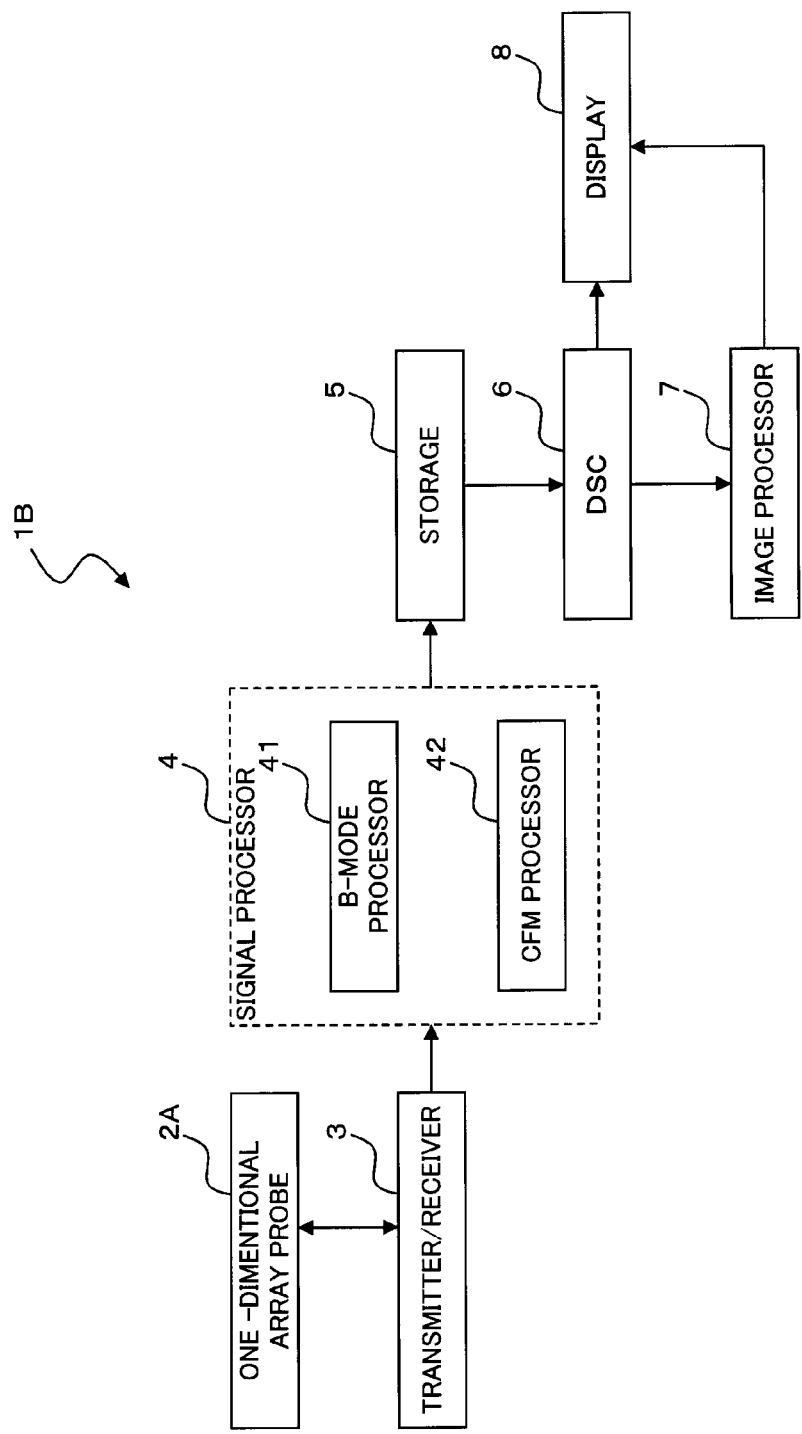
FIG. 17 is a block diagram showing an ultrasonic imaging apparatus according to a third embodiment of the present invention.
Figure 18A:
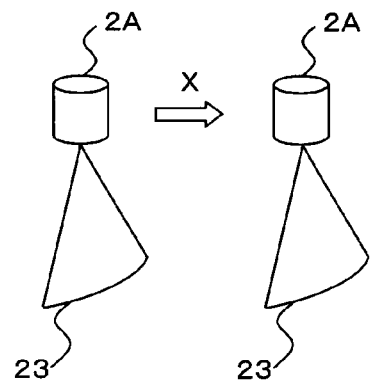
FIG. 18A is a schematic drawing showing a range of scanning by a one-dimensional array probe.
Figure 18B:
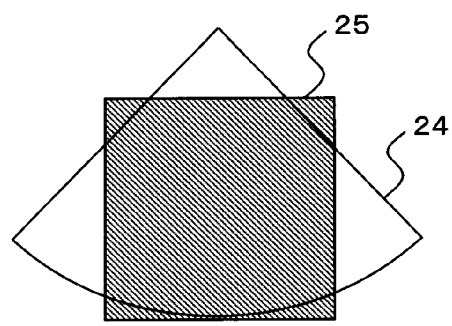
FIG. 18B is a schematic drawing showing a two-dimensional image.
Figure 18C:
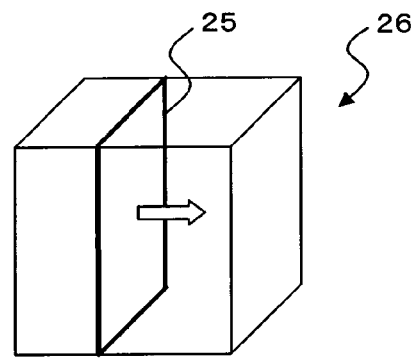
FIG. 18C is a schematic drawing showing voxel data.

Next, an ultrasonic imaging apparatus and an ultrasonic image-processing method according to the third embodiment of the present invention will be described referring to FIG. 17, FIG. 18A, FIG. 18B, and FIG. 18C. FIG. 17 is a block diagram showing an ultrasonic imaging apparatus according to the third embodiment of the present invention. FIG. 18A is a schematic drawing showing a range scanned by a one-dimensional array probe. FIG. 18B is a schematic drawing showing a two-dimensional image. FIG. 18C is a schematic drawing showing voxel data.

A one-dimensional array probe 2A is used in the ultrasonic imaging apparatus 1B according to the third embodiment. An operator manually moves the one-dimensional array probe 2A to scan a three-dimensional space with ultrasonic waves. As shown in FIG. 18A for example, the one-dimensional array probe 2A can scan inside a two-dimensional cross-section 23 with ultrasonic waves. Then, the operator manually moves the one-dimensional array probe 2A in a predetermined direction (x direction in the figure), thereby making it possible to scan a three-dimensional space with ultrasonic waves.

In the third embodiment, the DSC 6 generates two-dimensional image data by performing a two-dimensional scan conversion process. As shown in FIG. 18B for example, upon receiving two-dimensional scanning data 24 obtained two-dimensionally, the DSC 6 generates two-dimensional image data 25 by applying a two-dimensional scan conversion process to the three-dimensional scanning data 24. Then, the DSC 6 outputs the two-dimensional image data 25 to the image processor 7. In addition, the DSC 6 outputs the two-dimensional image data to the display 8. Consequently, a two-dimensional image (tomographic image), based on the two-dimensional image data will be displayed on the display 8.

Upon receiving a plurality of two-dimensional image data from the DSC 6, the image processor 7 generates voxel data 26 by combining the plurality of two-dimensional image data 25 as shown in FIG. 18C. The image processor 7 generates three-dimensional image data by applying volume rendering to the voxel data 26.

The image processor 7 has the same functions as the image processor 7 according to the first embodiment described above. That is, the image processor 7 applies a smoothing process to voxel data, and calculates the vector of each voxel based on the voxel data to which the smoothing process has been applied. Then, the image processor 7 generates shaded three-dimensional image data by applying a ray-tracing process to voxel data to which the smoothing process has not been applied, according to the vector. This enables a reduction of shadows as artifacts without reducing the space resolution of the three-dimensional image.

In addition, instead of the image processor 7, the image processor 7A according to the modification 1 may be installed on the ultrasonic imaging apparatus 1B. In this case, the image processor 7A calculates the vector of each voxel based on voxel data to which a smoothing process has not been applied, and calculates an average of a plurality of vectors included within a preset specified range. Then, image processor 7A generates shaded three-dimensional image data by applying a ray-tracing process to the voxel data to which the smoothing process has not bee applied, according to the vector. This enables a reduction of shadows as artifacts without reducing the space resolution of three-dimensional image.

The ultrasonic imaging apparatus 1B comprises the image processor 7 or image processor 7A in the third embodiment. In addition, the image processor or the DSC according to the modification 2 or the second embodiment may also be installed on the ultrasonic imaging apparatus 1B. In this case also, it becomes possible to reduce shadows as artifacts without reducing the space resolution of three-dimensional image.

Also in the third embodiment, as in the first embodiment, image data represented by a three-dimensional coordinate system other than the Cartesian coordinate system may be generated instead of voxel data.

Fourth Embodiment

Figure 19:
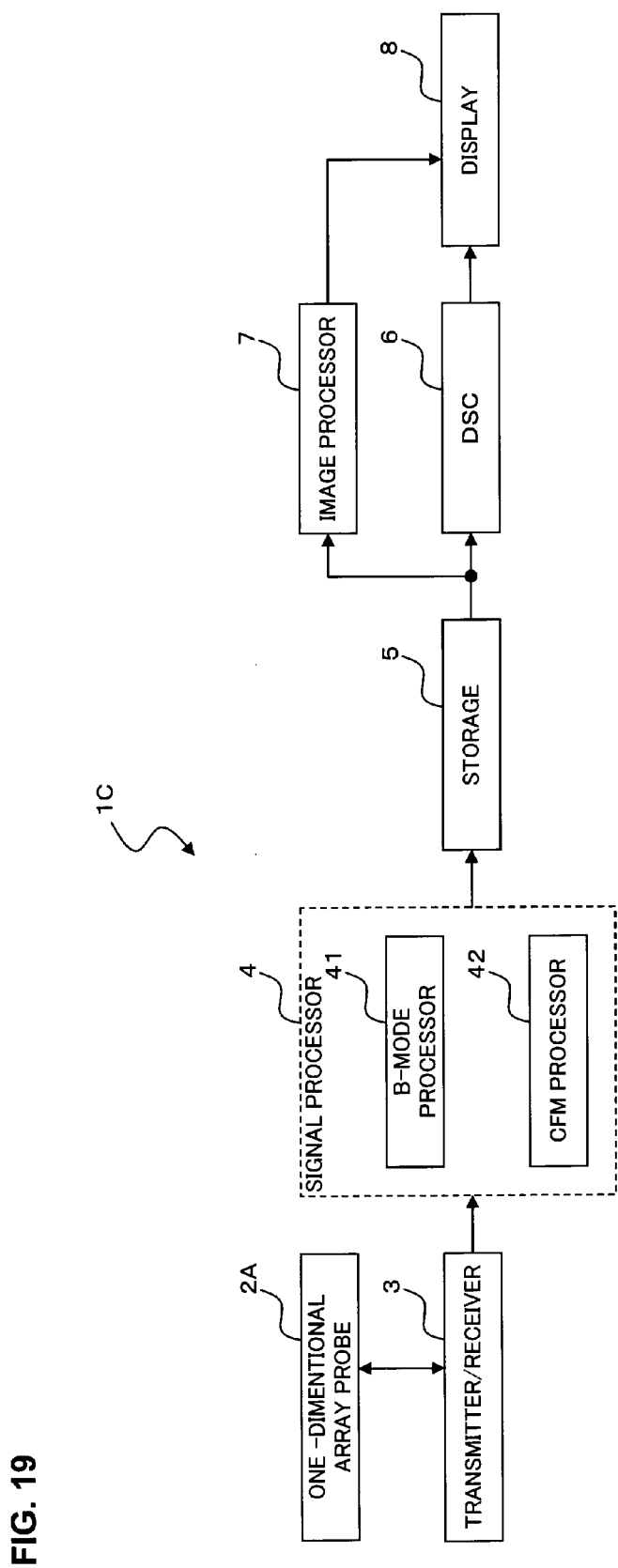
FIG. 19 is a block diagram showing an ultrasonic imaging apparatus according to a fourth embodiment of the present invention.

Next, an ultrasonic imaging apparatus and an ultrasonic image-processing method according to the fourth embodiment of the present invention will be described referring to FIG. 19. FIG. 19 is a block diagram showing an ultrasonic imaging apparatus according to the fourth embodiment of the present invention.

The one-dimensional array probe 2A is used in an ultrasonic imaging apparatus IC according to the fourth embodiment, as in the ultrasonic imaging apparatus 1B according to the third embodiment. In the fourth embodiment, the image processor 7 generates two-dimensional image data by performing a two-dimensional scan conversion process. Furthermore, the image processor 7 generates voxel data by combining a plurality of two-dimensional image data. Then, the image processor 7 generates three-dimensional image data by applying volume rendering to the voxel data.

The image processor 7 performs the same functions as the image processor 7 according to the first embodiment described above. That is, the image processor 7 applies a smoothing process to voxel data, and calculates the vector of each voxel, based on the voxel data to which the smoothing process has been applied. Then, the image processor 7 generates shaded three-dimensional image data by applying a ray-tracing process to voxel data to which the smoothing process has not been applied, according to the vector. This enables a reduction of shadows as artifacts without reducing the space resolution of the three-dimensional image.

In addition, as in the ultrasonic imaging apparatus 1B according to the third embodiment described above, instead of the image processor 7, the image processor 7A according to the modification 1 may be installed on the ultrasonic imaging apparatus 1C. In this case also, it becomes possible to reduce shadows as artifacts without reducing the space resolution of the three-dimensional image.

Moreover, also in the fourth embodiment, as in the first embodiment, image data represented by a three-dimensional coordinate system other than the Cartesian coordinate system may be generated instead of voxel data.

The ultrasonic imaging apparatus has been described in the embodiments or the modifications described above. However, the present invention is not limited to the ultrasonic imaging apparatus. Even when the image processor 7 or the like is applied to another medical image-processing apparatus such as an X-ray CT apparatus or an MRI apparatus, it is possible to achieve the same effects as the ultrasonic imaging apparatus 1 according to the first embodiment, and the like. Furthermore, the present invention may also be applied to an image-processing apparatus other than a medical image-processing apparatus. Examples of application of the present invention to a medical image-processing apparatus will be described in a fifth embodiment and a sixth embodiment.

Fifth Embodiment

Figure 20:
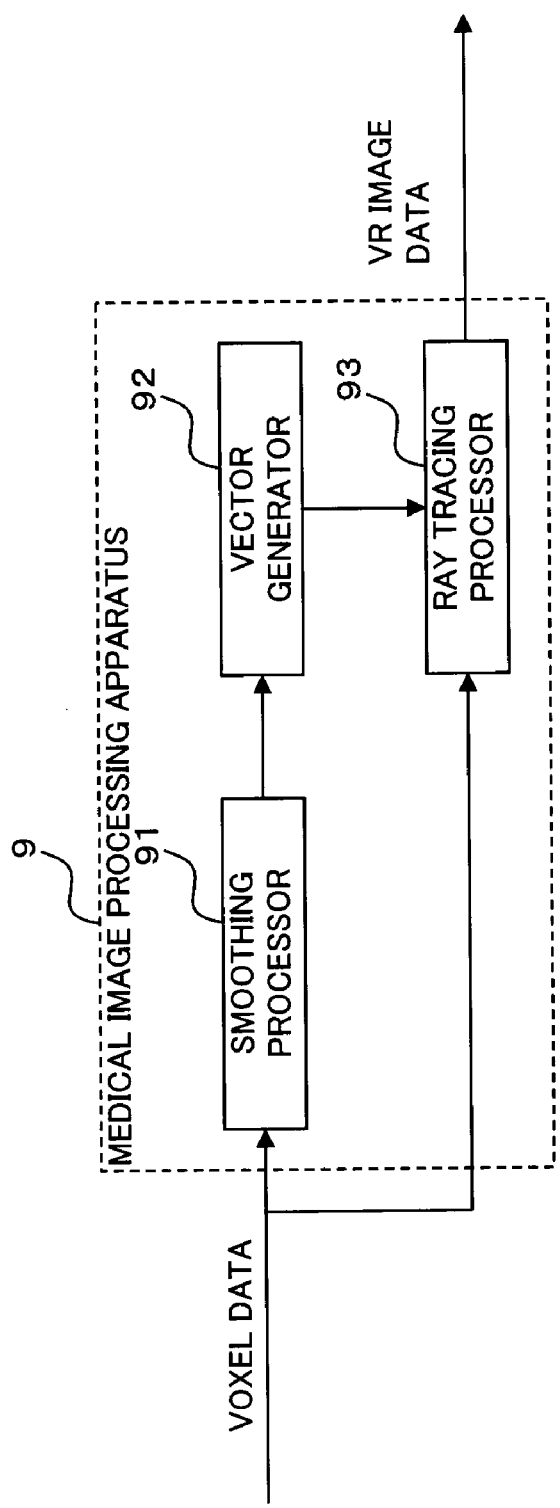
FIG. 20 is a block diagram showing a medical image-processing apparatus according to a fifth embodiment of the present invention.

An image-processing apparatus according to a fifth embodiment of the present invention will be described referring to FIG. 20. FIG. 20 is a block diagram showing an image-processing apparatus according to the fifth embodiment of the present invention.

An image-processing apparatus 9 comprises a smoothing processor 91, a vector generator 92, and a ray-tracing processor 93. The image-processing apparatus 9 receives voxel data from outside and applies volume rendering to the voxel data, thereby generating shaded three-dimensional image data. Each part of the image-processing apparatus 9 will be described below.

Upon receiving the voxel data from outside, the smoothing processor 91 applies a smoothing process to the voxel data by using a predetermined smoothing filter. Then, the smoothing processor 91 outputs the voxel data after the smoothing process to the vector generator 92. This voxel data after the smoothing process is used to calculate the vectors of voxels.

Upon receiving the voxel data after the smoothing process from the smoothing processor 91, the vector generator 92 finds the vector of each voxel, based on the voxel data. Then, the vector generator 92 outputs the vector to the ray-tracing processor 93.

Upon receiving voxel data to which the smoothing process has not been applied and furthermore receiving the vector from the vector generator 92, the ray-tracing processor 93 generates shaded three-dimensional image data by applying a ray-tracing process to the voxel data.

The ray-tracing processor 93 outputs the shaded three-dimensional image data to a not-shown display. A three-dimensional image based on the shaded three-dimensional image data is displayed on the display.

As described above, voxel data to which a smoothing process has not been applied is used as voxel data to be subjected to a ray-tracing process. In addition, voxel data to which a smoothing process has been applied is used as voxel data for finding the vector of voxels. Consequently, it becomes possible to reduce shadows as artifacts without reducing the space resolution of three-dimensional image data.

In the fifth embodiment, a smoothing process may also be performed twice as in the modification 3 described above. For example, the smoothing processor 91 applies the first smoothing process to voxel data. Furthermore, the smoothing processor 91 applies the second smoothing process in which smoothing action is stronger than the first smoothing process, to the voxel data to which the first smoothing process has been applied. Then, the smoothing processor 91 outputs the voxel data to which the first smoothing process has been applied, to the ray-tracing processor 93. In addition, the smoothing processor 91 outputs the voxel data to which the first and second smoothing processes have been applied, to the vector generator 92. Performing a plurality of smoothing processes on voxel data used in calculation of the vector makes it possible to prevent the vector from abruptly changing. In addition, only a smoothing process to remove noise at most is applied to the voxel data subjected to the ray-tracing process, whereby the reduction of space resolution of three-dimensional image data is avoided.

Moreover, also in the fifth embodiment, as in the first embodiment, image data represented by a three-dimensional coordinate system other than the Cartesian coordinate system may be generated instead of voxel data.

Sixth Embodiment

Figure 21:
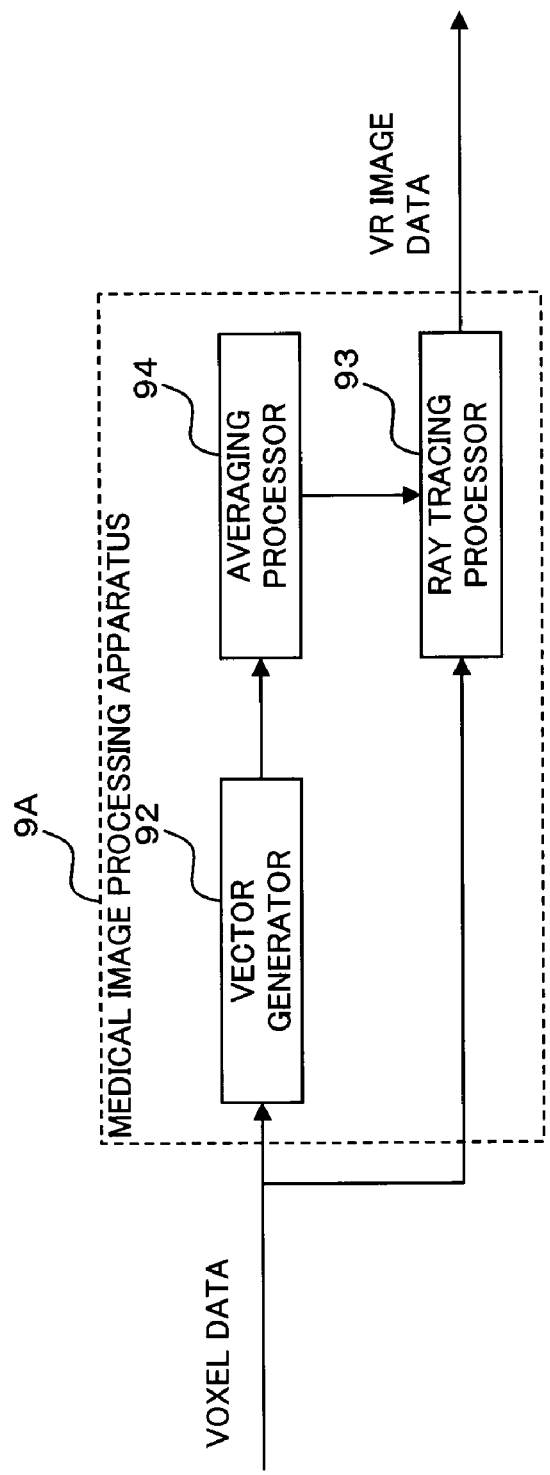
FIG. 21 is a block diagram showing a medical image-processing apparatus according to a sixth embodiment of the present invention.

Next, an image-processing apparatus according to the sixth embodiment of the present invention will be described referring to FIG. 21. FIG. 21 is a block diagram showing an image-processing apparatus according to the sixth embodiment of the present invention.

An image-processing apparatus 9A comprises the vector generator 92, the ray-tracing processor 93, and an averaging processor 94. The image-processing apparatus 9A receives voxel data from outside and applies volume rendering to the voxel data, thereby generating shaded three-dimensional image data. Each part of the image-processing apparatus 9A will be described below.

Upon receiving the voxel data from outside, the vector generator 92 finds the vector of each voxel, based on the voxel data. Then, the vector generator 93 outputs the vector to the averaging processor 94.

Upon receiving the vector from the vector generator 92, the averaging processor 94 calculates an average of vectors for a plurality of vectors included within a preset specified range. Consequently, the averaging processor 94 averages the vectors of the respective voxels. Then, the averaging processor 94 outputs the averaged vector to the ray-tracing processor 74.

Upon receiving the voxel data from outside and furthermore receiving the vector of each voxel from the averaging processor 94, the ray-tracing processor 93 generates three-dimensional image data by applying a ray-tracing process to the voxel data. In the sixth embodiment, the voxel data output to the ray-tracing processor 93 is not subjected to a smoothing process. On the other hand, the vector output from the averaging processor 94 to the ray-tracing processor 93 is averaged by the averaging processor 94. Then, the ray-tracing processor 93 generates shaded three-dimensional image data by applying a ray-tracing process to the voxel data to which a smoothing process has not been applied, according to the averaged vector.

The ray-tracing processor 93 outputs the shaded three-dimensional image data to a not-shown display. Consequently, a three-dimensional image based on the shaded three-dimensional image data is displayed on the display.

As described above, voxel data to which a smoothing process has not been applied is used as voxel data to be subjected to a ray-tracing process. In addition, averaged vector is used for a ray-tracing process. Consequently, it becomes possible to reduce shadows as artifacts without reducing the space resolution of three-dimensional image data.

In the sixth embodiment, as in the first embodiment, image data represented by a three-dimensional coordinate system other than the Cartesian coordinate system may be generated instead of voxel data.

What is claimed is:

1. An ultrasonic imaging apparatus, comprising:
    a scanner configured to transmit ultrasonic waves to a subject to be examined and receive reflected waves from said subject to be examined, so as to obtain scanning data;
    a converter configured to convert said scanning data into image data represented by a predetermined three-dimensional coordinate system;
    a vector generator configured to calculate a normal vector indicating a normal orientation of a region forming said image data based on said scanning data or said image data;
    a smoothing processor configured to apply a smoothing process to said scanning data, said image data, or said normal vector; and
    a three-dimensional image generator configured to generate three-dimensional image data based on an orientation of the normal vector generated based on the smoothed scanning data, an orientation of the normal vector generated based on the smoothed image data or the smoothed normal vector, further based on the image data before application of the smoothing processing.

2. The ultrasonic imaging apparatus according to claim 1, wherein:
    said smoothing processor is configured to apply a smoothing process to said image data;
    said vector generator is configured to calculate a point normal vector of each point constituting said image data, based on said image data to which said smoothing process has been applied; and
    said three-dimensional image generator is configured to generate three-dimensional image data by applying a ray-tracing process to the image data before application of the smoothing processing according to the orientation of said normal vector.

3. The ultrasonic imaging apparatus according to claim 2, wherein:
    said converter converts said scanning data into voxel data represented by a Cartesian coordinate system;
    said smoothing processor applies a smoothing process to said voxel data;
    said vector generator calculates a voxel normal vector regarding each voxel constituting said voxel data, based on the voxel data to which said smoothing process has been applied; and
    said three-dimensional image generator generates three-dimensional image data by applying a ray-tracing process to the voxel data before application of the smoothing processing, according to the orientation of said normal vector.

4. The ultrasonic imaging apparatus according to claim 1, wherein:
    said smoothing processor comprises an averaging processor configured to determine an averaged normal vector by calculating a weighted average of a plurality of normal vectors included within a predetermined range; and
    said three-dimensional image generator is configured to generate three-dimensional image data by applying a ray-tracing process to said image data, according to an orientation of said averaged normal vector.

5. The ultrasonic imaging apparatus according to claim 4, wherein:
    said converter converts said scanning data into voxel data represented by a Cartesian coordinate system;
    said vector generator calculates a voxel normal vector regarding each voxel constituting said voxel data, based on said voxel data;
    said averaging processor averages the voxel normal vector regarding each voxel, by calculating the weighted average of the voxel normal vectors for the plurality of voxel normal vectors included within said predetermined range; and
    said three-dimensional image generator generates three-dimensional image data by applying a ray-tracing process to said voxel data, according to the orientation of said averaged normal vector.

6. The ultrasonic imaging apparatus according to claim 1, wherein:
    said smoothing processor is configured to apply a smoothing process to said scanning data;
    said converter is configured to convert the scanning data before application of the smoothing processing into first image data represented by a predetermined three-dimensional coordinate system, and to convert the scanning data to which said smoothing process has been applied into second image data represented by a predetermined three-dimensional coordinate system;

said vector generator is configured to calculate a second normal vector indicating a normal orientation of a region constituting said second image data, based on said second image data; and said three-dimensional image generator is configured to generate the three-dimensional image data by applying a ray-tracing process to said first image data, according to the orientation of said second normal vector.

7. The ultrasonic imaging apparatus according to claim 6, wherein:

said converter converts the scanning data before application of the smoothing processing, into first voxel data represented by a Cartesian coordinate system, and converts the scanning data to which said smoothing process has been applied into second voxel data represented by the Cartesian coordinate system;

said vector generator calculates a voxel normal vector regarding each voxel constituting said second voxel data, based on said second voxel data; and said three-dimensional image generator generates the three-dimensional image data by applying a ray-tracing process to said first voxel data, according to the orientation of said normal vector.

8. The ultrasonic imaging apparatus according to claim 1, further comprising a first smoothing processor configured to apply a first smoothing process to said image data, wherein said smoothing processor comprises a second smoothing processor configured to apply a second smoothing process to the image data to which said first smoothing process has been applied;

said vector generator is configured to calculate said normal vector, based on the image data to which said second smoothing process has been applied; and said three-dimensional image generator is configured to generate said three-dimensional image data by applying a ray-tracing process to the image data to which said first smoothing process has been applied, according to the orientation of said normal vector.

9. The ultrasonic imaging apparatus according to claim 8, wherein:

said converter converts said scanning data into voxel data represented by a Cartesian coordinate system;

said first smoothing processor applies the first smoothing process to said voxel data;

said second smoothing processor applies the second smoothing process to the voxel data to which said first smoothing process has been applied;

said vector generator calculates a voxel normal vector regarding each voxel constituting said voxel data, based on the voxel data to which said second smoothing process has been applied; and said three-dimensional image generator generates the three-dimensional image data by applying a ray-tracing process to the voxel data to which said first smoothing process has been applied, according to the orientation of said normal vector.

10. The ultrasonic imaging apparatus according to claim 9, wherein:

said second smoothing processor applies said second smoothing process to the voxel data to which said first smoothing process has been applied, by using a smoothing filter stronger than a smoothing filter used in said first smoothing processor.

11. An image-processing apparatus, comprising:

a vector generator configured to receive image data represented by a predetermined three-dimensional coordinate system to calculate a normal vector indicating a normal orientation of a region forming image data;

a smoothing processor configured to apply a smoothing process to said image data or said normal vector; and three-dimensional image generator configured to generate three-dimensional image data based on the image data before application of the smoothing processing, further based on an orientation of said normal vector generated based on the smoothed image data or an orientation of said smoothed normal vector.

12. The image-processing apparatus according to claim 11, wherein:

said vector generator is configured to calculate a point normal vector regarding each point constituting said image data based on the image data to which said smoothing process has been applied; and said three-dimensional image generator is configured to generate the three-dimensional image data by applying a ray-tracing process to the image data before application of the smoothing processing, according to the orientation of said normal vector.

13. The image-processing apparatus according to claim 11, wherein:

said vector generator is configured to receive image data represented by said predetermined three-dimensional coordinate system and calculate a point normal vector regarding each point constituting said image data;

said averaging processor is configured to determine an averaged normal vector by calculating a weighted average of a plurality of the point normal vectors included within a predetermined range; and said three-dimensional image generator is configured to generate the three-dimensional image data by applying a ray-tracing process to said image data, according to the orientation of said averaged normal vector.

14. The image-processing apparatus according to claim 11, further comprising:

a first smoothing processor configured to receive image data represented by said predetermined three-dimensional coordinate system and apply a first smoothing process to said image data, wherein said smoothing processor comprises a second smoothing processor configured to apply a second smoothing process to the image data to which said first smoothing process has been applied;

said vector generator is configured to calculate said normal vector based on the image data to which said second smoothing process has been applied; and the three-dimensional image generator is configured to generate the three-dimensional image data by applying a ray-tracing process to the image data to which said first smoothing process has been applied, according to the orientation of said normal vector.

15. An ultrasonic image-processing method, comprising:

obtaining scanning data by transmitting ultrasonic waves to a subject to be examined and receiving reflected waves from said subject to be examined;

converting said scanning data into image data represented by a predetermined three-dimensional coordinate system;

calculating a normal vector indicating a normal orientation of a region forming said image data based on said scanning data or said image data;

applying a smoothing process to said scanning data, said image data, or said normal vector; and generating three-dimensional image data based on an orientation of the normal vector generated based on the smoothed scanning data, an orientation of the normal vector generated based on the smoothed image data, or the smoothed normal vector, further based on the image data before application of the smoothing processing.

16. The ultrasonic image-processing method according claim 15, wherein:

said step of applying the smoothing process comprises applying a smoothing process to said image data;

said calculating step comprises calculating a point normal vector of each point constituting said image data based on the image data to which said smoothing process has been applied; and said generating step comprises generating the three-dimensional image data by applying a ray-tracing process to the image data before application of the smoothing processing, according to an orientation of said normal vector.

17. The ultrasonic image-processing method according claim 15, wherein:

the step of applying the smoothing process comprises determining an averaged normal vector by calculating a weighted average of a plurality of other normal vectors included within a predetermined range; and the generating step comprises generating the three-dimensional image data by applying a ray-tracing process to said image data, according to an orientation of said averaged normal vector.

18. The ultrasonic image-processing method according to claim 15, wherein:

said step of applying the smoothing processing comprises applying a smoothing process to said scanning data;

said converting step comprises converting the scanning data before application of the smoothing processing, into first image data represented by a predetermined three-dimensional coordinate system, and converting the scanning data to which said smoothing process has been applied, into second image data represented by a predetermined three-dimensional coordinate system;

said calculating step comprises calculating a second normal vector indicating a normal orientation of a region constituting said second image data based on said second image data; and said generating step comprises generating the three-dimensional image data by applying a ray-tracing process to said first image data, according to the orientation of said second normal vector.

19. The ultrasonic image-processing method according to claim 15, wherein:

said step of applying the smoothing processing comprises applying a first smoothing process to said image data, and applying a second smoothing process to the image data to which said first smoothing process has been applied;

said calculating step comprises calculating a second normal vector based on the image data to which said second smoothing process has been applied; and said generating step comprises generating the three-dimensional image data by applying a ray-tracing process to the image data to which said first smoothing process has been applied, according to an orientation of said second normal vector.

* * * * *